United States Patent
Smallwood

(10) Patent No.: US 9,875,514 B2
(45) Date of Patent: Jan. 23, 2018

(54) SYSTEM AND METHODS FOR MANAGING PATIENTS AND SERVICES

(76) Inventor: William Smallwood, Ashburn, VA (US)

(*) Notice: Subject to any disclaimer, the term of this patent is extended or adjusted under 35 U.S.C. 154(b) by 448 days.

(21) Appl. No.: 13/287,591

(22) Filed: Nov. 2, 2011

(65) Prior Publication Data

US 2013/0110545 A1 May 2, 2013

(51) Int. Cl.
*G06F 19/00* (2011.01)
*H04M 11/00* (2006.01)
*G06Q 50/24* (2012.01)
*G06Q 10/10* (2012.01)

(52) U.S. Cl.
CPC .......... *G06Q 50/24* (2013.01); *G06F 19/327* (2013.01); *G06Q 10/109* (2013.01)

(58) Field of Classification Search
CPC ...... G06Q 50/22; G06Q 50/24; G06F 19/322; G06F 19/3418; G06F 19/327; G06F 19/3462; H04M 11/00
USPC .......................................................... 705/3
See application file for complete search history.

(56) References Cited

U.S. PATENT DOCUMENTS

| | | | | |
|---|---|---|---|---|
| 7,813,939 B2* | 10/2010 | Clements et al. | ................ | 705/2 |
| 7,912,733 B2* | 3/2011 | Clements et al. | ................ | 705/2 |
| 8,086,473 B2* | 12/2011 | Oh | ................... | 705/3 |
| 8,441,353 B2* | 5/2013 | Williams et al. | .......... | 340/572.1 |
| 2006/0047529 A1 | 3/2006 | Fahimi | | |
| 2007/0255586 A1* | 11/2007 | Green et al. | ...................... | 705/2 |
| 2008/0033754 A1 | 2/2008 | Smith | | |
| 2009/0198514 A1 | 8/2009 | Rhodes | | |

* cited by examiner

*Primary Examiner* — Hiep V Nguyen
(74) *Attorney, Agent, or Firm* — Attentive Law Group; Paul Ratcliffe

(57) ABSTRACT

A system and methods for monitoring compliance with at least one time based rule for treating individuals with health related procedure requests. The system includes a server which periodically receives information on individuals within a group, a request procedure type, and a request date for the individuals that requested a health related procedure. The system then tracks the lapsed time of each health related request to monitor compliance with the time based rule. The system can also rank the individuals for scheduling of the health related procedure based on the procedure type, lapsed time, and the time based rule. The server also identifies individuals which have changed facilities while maintaining their original request date and then updates the rankings for each facility. The system is especially useful for handling dental procedures and requests for individuals at correctional institutions, military bases, and campuses.

23 Claims, 20 Drawing Sheets

SYSTEM AND METHODS FOR MANAGING PATIENTS AND SERVICES

BACKGROUND OF THE INVENTION

1. Field of the Invention

The present invention relates generally to a system and method for managing and administering patients, time based rules and personnel across one or more facilities. The present invention is ideally suited for use in correctional institutions. More particularly, the invention relates to a system and method for scheduling, tracking, and managing requests, grievances, personnel, supplies, and facilities for health and, specifically, dental activities within a correctional institution.

2. Description of the Related Art

Prisons or correctional institutions have unique factors to contend with when handling the care and treatment of inmates. Included in this care and treatment are the inmate's physical health, mental health, pharmaceutical, and dental care needs. Therefore, correctional institutions need doctors, psychiatrists, physician assistants, pharmacists, dentists, dental assistants, and hygienists to perform many intensive and time-sensitive procedures on patients. However, these same institutions have numerous factors to account for when treating inmates including safety, security, scheduling, lockdowns, transfers, health standards, release dates and more. These factors create a need for prison facilities to manage their dental operations effectively.

The majority of correctional health and dental departments currently rely on paper scheduling systems to manage their health and dental operations. These inefficient systems often result in institutions not meeting standards established by the respective Department of Corrections and governing bodies including the American Correctional Association and National Commission on Correctional Health Care.

One of the important standards includes the number of days by which service should be rendered based on the date the procedure was requested, referred to herein as the "Lapse Time" or "Lapsed Time". More specifically, the Lapse Time refers to the number of days the service should be rendered starting from the date the service was requested. Adhering to such standards prevents or limits grievances and ensuing law suits. However, current health and dental management systems are focused on scheduling and treating typical or standard patients and do not account for the unique factors and standards of correctional institutions. What is needed is a system which helps administer health, mental health, and dental practices for correctional facilities by tracking and scheduling treatment requests while adhering to the unique standards and issues of correctional institutions.

SUMMARY OF THE INVENTION

This summary is provided to introduce concepts in a simplified form that are further described in the detailed description of the invention. This summary is not intended to identify key or essential inventive concepts of the claimed subject matter, nor is it intended for determining the scope of the claimed subject matter.

The present invention provides a computer or web-based system designed for maximum efficiency in the scheduling and tracking of health care, mental health care, pharmacy care, and correctional dentistry. Health and mental health care are referred to herein collectively as health care. The software of the present invention has the ability to: (1) Track and log all health care and dental requests received; (2) Schedule patients; (3) Track health care and dental services delivered; (4) Track Lapse Times; (5) Provide Alerts for impending or missed Lapse Times; (6) Compile utilization reports; (7) Monitor off-site health care and dental care referrals/transportation issues; (8) Track ongoing specialty and prosthetic cases to ensure timely delivery; (9) Track grievances from initiation through closure; (10) automate scheduling; (11) Handle inmate transfers; (12) Handle prison lockdowns and interruptions; and (13) Numerous reporting capabilities The system can simultaneously schedule multiple doctors, physician assistants, dentists and dental hygienists at each location and adjust scheduling accordingly. In addition, the system has numerous "time triggers" or alerts for notifying users of deadlines, approaching treatments and late procedures. The software of the present invention also keeps track of time periods specific to each procedure. Patient or inmate information is updated on a daily bases.

The system and software can function as a standalone system, Local Area Network (LAN), Wide Area Network (WAN), or as a web based application.

The system is comprised of a server with one or more computer programs configured to monitor compliance with at least one time based rule; wherein the server: (1) receives information on a periodic basis on a plurality of individuals within a group from at least one facility, wherein the information includes an identification element and a facility identifier for each individual within the group, and a request procedure type and a request date for each individual within the group that has requested a health related procedure; (2) tracks the lapsed time of each health related request for each individual starting from the request date to monitor compliance with the at least one time based rule; wherein the at least one time based rule is based on the procedure type; and (3) ranks the individuals within each of the at least one facility for scheduling of the health related procedure based on the procedure type, lapsed time and the at least one time based rule. The server also processes the information against previously received information to identify individuals within the group which have a facility identifier change indicating the individual has changed facilities; and updates the ranking of individuals within each at least one facility for scheduling of the health related procedure based on the lapsed time and the at least one time based rule; wherein the individuals which have transferred facilities maintain their original health related procedure request date. The system is ideally suited for inmates at correctional institutions, soldiers at military bases, and students at campuses. The system of the present invention is ideal for dental procedures.

Further, the one or more time based rules are typically the number of days from the request date by which a procedure should be performed based on the procedure type. The number of days can be set by an administrative user of the system. Data related to identified and ranked individuals for scheduling can be transmitted to a remote device for display to a user where the user can select at least one individual to be added to a schedule. The system provides an alert when the lapsed time exceeds the time based rule. The alert can be an identifier displayed on a graphical user interface or can be an email or text message sent to an identified address. Ideally, the system receives information on new patients (inmates) on a daily basis. The system of the present invention may also automatically generate a schedule based on the rankings.

The present invention also provides a system comprising a server with one or more computer programs configured to monitor compliance with at least one time based rule;

wherein the server: (1) receives information on a periodic basis on a plurality of individuals within a group from at least one facility, wherein the information includes an identification element and a facility identifier for each individual within the group, and a request procedure type and a request date for each individual within the group that has requested a health related procedure; (2) tracks the lapsed time of each health related request for each individual starting from the request date to monitor compliance with the at least one time based rule; wherein the at least one time based rule is based on the procedure type; (3) ranks the individuals within each of the at least one facility for scheduling of the health related procedure based on the procedure type, lapsed time and the at least one time based rule; (4) processes the information against previously received information to identify individuals within the group which have a facility identifier change indicating the individual has changed facilities; and (5) updates the ranking of individuals within each facility for scheduling of the health related procedure based on the lapsed time and the at least one time based rule; wherein the individuals which have transferred facilities maintain their original health related procedure request date; wherein the at least one time based rule is the number of days from the request date by which a procedure should be performed based on the procedure type; wherein data related to the identified and ranked individuals for scheduling are transmitted to a remote device for display to a user and the user can select at least one individual to be added to a schedule; and wherein the system provides an alert when the lapsed time exceeds the time based rule.

The present invention further provides a system comprising: a server with one or more computer programs configured to monitor compliance with at least one time based rule; wherein the server (1) receives information on a periodic basis on a plurality of individuals within a group from at least one facility, wherein the information includes an identification element and a facility identifier for each individual within the group, and a request procedure type and a request date for each individual within the group that has requested a health related procedure; (2) tracks the lapsed time of each health related request for each individual starting from the request date to monitor compliance with the at least one time based rule; wherein the at least one time based rule is based on the procedure type; (3) determines a set of individuals within each facility for scheduling of the health related procedure based on the procedure type, lapsed time and the at least one time based rule; (4) identifies individuals within the group which have a facility identifier change indicating the individual has changed facilities; and (5) updates the determined set of individuals within each of the at least one facility for scheduling of the health related procedure based on the lapsed time and the at least one time based rule; wherein the individuals which have transferred facilities maintain their original health related procedure request date.

The present invention also provides a computer implemented method to monitor compliance with at least one time based rule, the method comprising: (1) receiving information on a periodic basis on a plurality of individuals within a group from at least one facility, wherein the information includes an identification element and a facility identifier for each individual within the group, and a request procedure type and a request date for each individual within the group that has requested a health related procedure; (2) assigning the at least one time based rule to each health related request for each individual; wherein the at least one time based rule is based on procedure type; (3) tracking the lapsed time of each health related request for each individual starting from the request date; and (4) ranking the individuals within the at least one facility based on the procedure type, the lapse timed, and the at least one time based rule. The method is ideally suited for inmates at a correctional institution; soldiers at a military base; or students on a campus. Further, the system is ideally suited for dental related procedures. The time based rule may be the number of days from the request date by which a procedure should be performed based on the procedure type which may be based on input received from an administrative user of the system. The method may also include the step of tracking the schedule of a medical professional wherein the schedule includes available and unavailable time slots and allows the user to set or select time slots on the schedule which are available or unavailable. The method further includes the step of scheduling the individuals based on the rank, procedure type, and available time slots and may also automatically generating a schedule of procedures based on the rankings. The method may further including the step of transmitting data related to the identified and ranked individuals for scheduling to a remote device for display to a user wherein the user can monitor and track the patient information, the lapse time for each health related request, and the scheduled individuals using the remote device. The method further includes the step of receiving an input from the user for the selection of an individual to be added to the schedule. The method can also include the step of identifying individuals whose lapsed time exceeds the time based rule and then alerting the user when the lapsed time exceeds the time based rule. The alert can be an identifier on the graphical user interface or can be an email or text message sent to an identified address.

The present invention also provides a computer implemented method to monitor the compliance with at least one time based rule, the method comprising: (1) receiving information on a periodic basis on a plurality of individuals within a group from at least one facility, wherein the information includes an identification element and a facility identifier for each individual within the group, and a request procedure type and a request date for each individual within the group that has requested a health related procedure; (2) assigning the at least one time based rule to each health related request for each individual; wherein the at least one time based rule is based on procedure type; (3) tracking the lapsed time of each health related request for each individual starting from the request date to monitor compliance with the at least one time based rule; wherein the at least one time based rule is based on the procedure type; (4) ranking the individuals with each facility based on the procedure type, lapse time, and the at least one time based rule; (5) determining a set of individuals within each facility for scheduling of the health related procedure based on the procedure type, lapsed time and the at least one time based rule; (6) identifying individuals within the group which have a facility identifier change indicating the individual has changed facilities; and (7) updating the ranking of individuals within each facility for scheduling of health related procedure based on the lapsed time and the at least one time based rule; wherein the individuals which have transferred facilities maintain their original health related procedure request date.

These and other objects, features, and/or advantages may accrue from various aspects of embodiments of the present invention, as described in more detail below.

BRIEF DESCRIPTION OF THE DRAWINGS

The foregoing summary, as well as the following detailed description of the invention, is better understood when read in conjunction with the appended drawing. For the purpose of illustrating the invention, exemplary constructions of the invention are shown in the drawings. However, the invention is not limited to the specific methods and instrumentalities disclosed herein.

FIG. 8 illustrates a graphical user interface of the Schedule Management display in accordance with the present invention;

FIG. 9 illustrates a graphical user interface of the Utilization Management display in accordance with the present invention;

FIG. 13 illustrates a graphical user interface for the Management Summary display in accordance with the present invention;

FIG. 14 illustrates a graphical user interface for the Utilization Detail display in accordance with the present invention;

FIG. 15 illustrates a graphical user interface for the Utilization Summary display in accordance with the present invention;

FIG. 16 illustrates a graphical user interface for the Transfer Report display in accordance with the present invention;

FIG. 18 illustrates a graphical user interface for the Lapse Time Management display for a particular institution in accordance with the present invention;

DETAILED DESCRIPTION OF EXEMPLARY EMBODIMENTS

Figure 1:
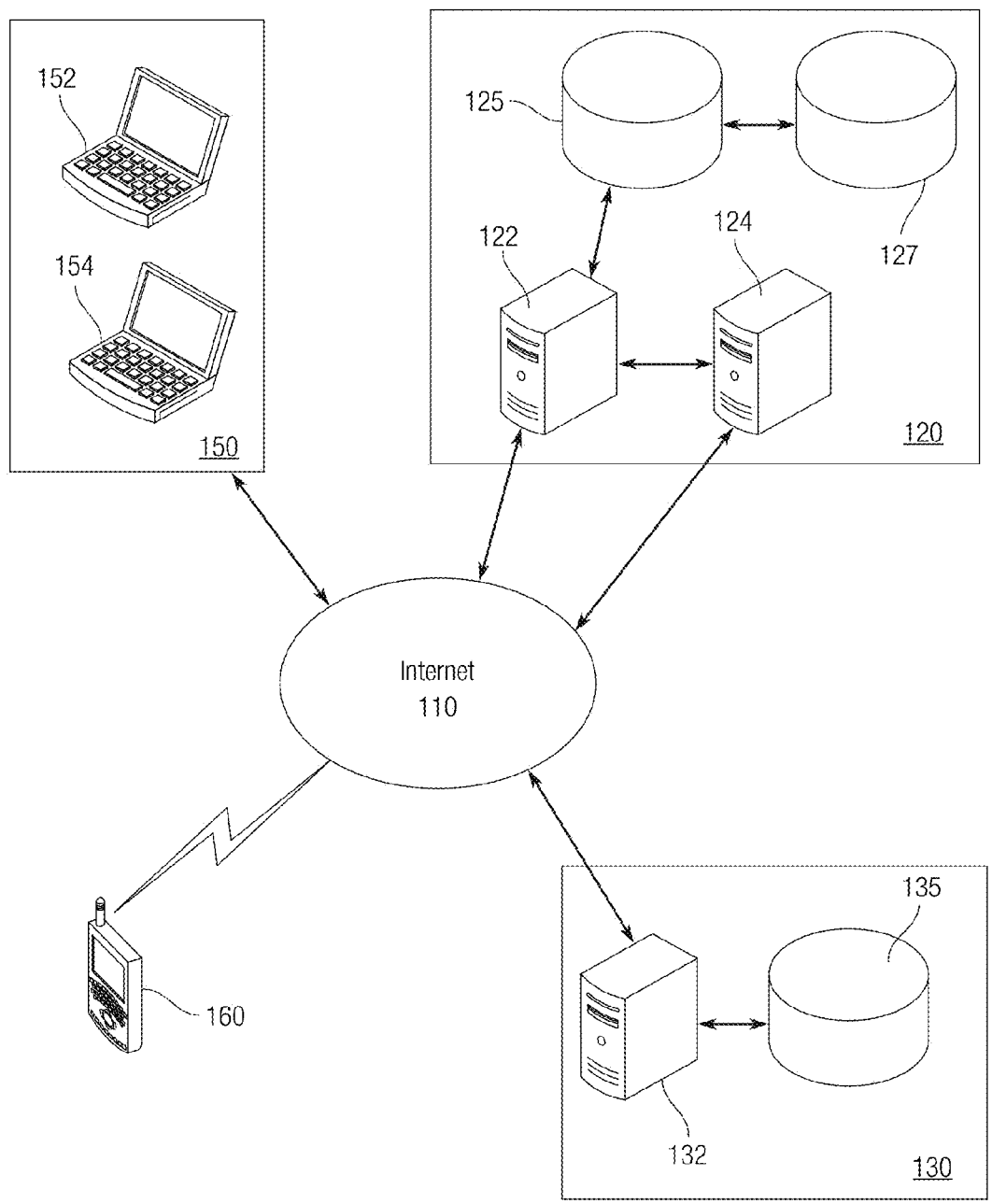
FIG. 1 illustrates a system diagram of the present invention including the main computer system, the correctional facility system, and access by remote users.

Particular embodiments of the present invention will now be described in greater detail with reference to the figures.

A system and methods for managing health care and dental operations in correctional environments is provided which employs various servers, computers, databases and applications allowing administrative users to manage correctional dental services while meeting compliance and standards issues. In most instances, each state sets their own health, mental health, and dental compliance regulations and standards with guidance provided by such organizations as the American Correctional Association (ACA) and the National Commission on Correctional Health Care (NC-CHC). Each correctional institution within a state tries to adhere to these standards to remain in compliance with the states established standards. Many of these standards dictate the time period for administering care to the inmates based upon the type of services needed. However, with the large and shifting population of correctional institutions it is hard to track the dates established by these standards while also maintaining a service request, scheduling, and management platform. Additionally, there is currently no system to track service requests against these standards, except for tracking by hand using a paper and pencil.

In a preferred embodiment, the present invention provides a main computer system 130 which accounts for such standards and dates through the use of various applications resident on one or more servers 132. The server 132 is connected to one or more databases 135. The main computer system 130 is accessible over the internet 110 by remote users in one or more locations 150 through their computers 152, 154. The system may also be accessed through a user's smart phone 160.

The main computer system 130 is also in communication with one or more systems of correctional institutions 120. Such communication may also be over the internet 110 or other communication path. The interaction between the main computer system 130 and the correctional facility system 120 enables the requests, services, and other features of the present invention to be tracked and analyzed for reporting and determining opportunities to increase efficiencies and avoid problems. The main computer system 130 also interacts with the correction system 120 to track or obtain current information on inmates, service requests, services rendered, and grievances.

The correctional facility system 120 may be comprised on one or more servers 122 which may be connected to one or more databases 125, 127. The correctional facility system 120 may also have local users on their computers 124 which are connected to the servers 122 and the internet 110.

By way of example, an user, such as an Senior Management user for a prison dental group, using a computer or other communication device 152, 154 to connect to the Internet or World Wide Web 110 can access the main computer system 130 of the present invention from a remote location. In the past, the user would have to drive to each facility to review and manage each facility's progress. With the present invention, the user is able to manage large scale health care and dental operations by tracking health care and dental treatment requests, creating or logging health care and dental treatment requests, scheduling health care and dental treatment appointments, and reviewing analytics and reports.

The main computer system 130 may comprise of one or more servers or computers 132 and one or more databases 135. The server 132 will contain the software and applications which provide access to the website, software applications, files, and one or more databases 135. A computer system includes the computer along with any software and peripheral devices. The computer would have an operating system, input devices such as a keyboard or mouse, memory, graphics capabilities, communication components such as a wireless interface device, and may include output devices. Such memory may be random access memory (RAM), non-transitory computer readable memory, or hard disc memory, Such memory would also store executable software.

Figure 2:
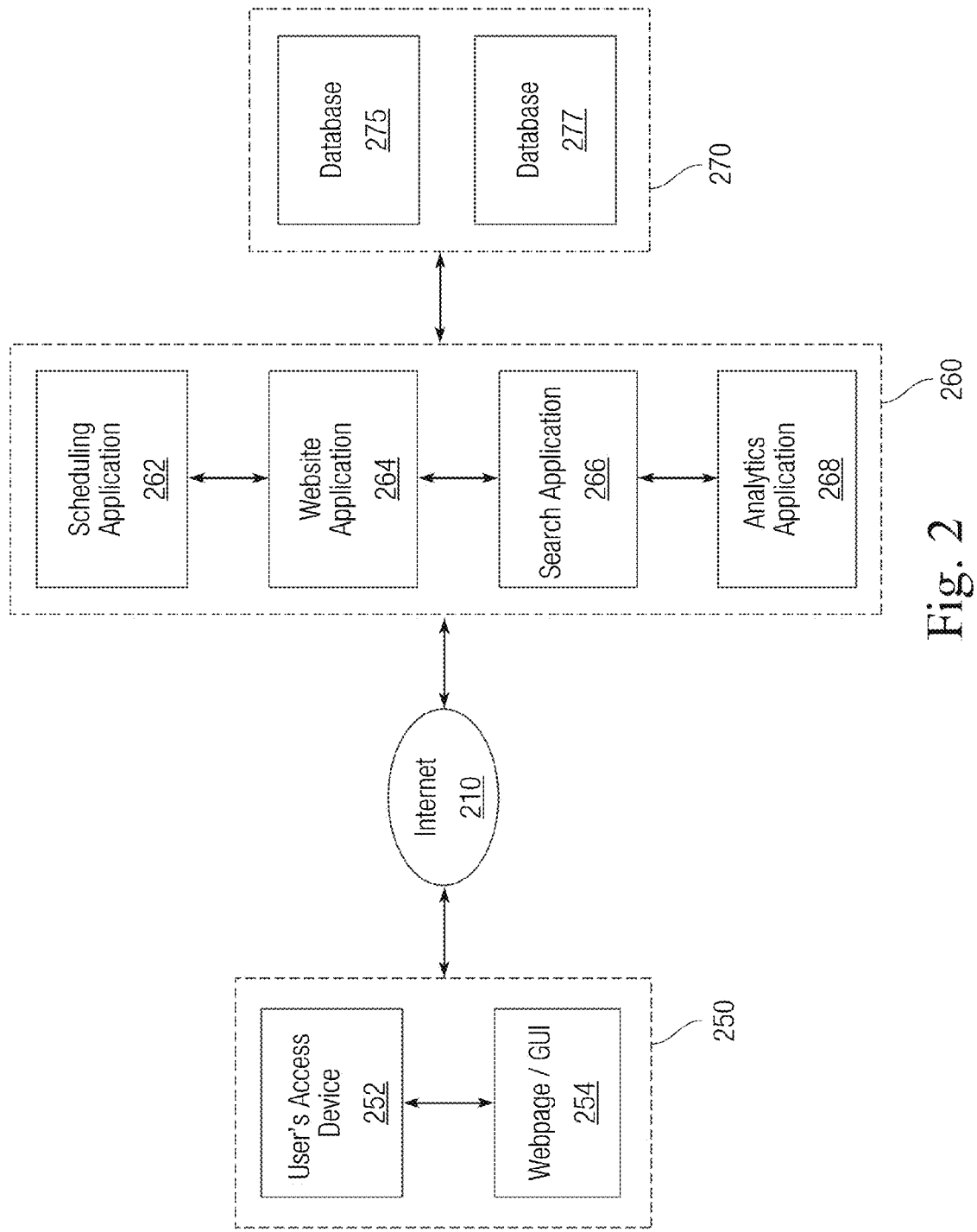
FIG. 2 illustrates a system diagram of the present invention at the application level.

FIG. 2 depicts the software and applications 260 resident on the main computer system which include, but are not limited to, a Website Application 264 and software applications such as, but not limited to, Scheduling Application 262, Search Application 266, and Analytics Application 268. The software and applications 260 provide access to one or more databases 270 which may include an inmate data and request information database 275 and a database comprised of Lapse Times, standards, and schedules for the various dentists and hygienists 277.

The software and applications 260 are accessible over the internet 210 by remote users through their user access devices 252, such as computers or smart phones, and through a webpage or graphic user interface of the system 254.

By way of example, a user may use his computer or smart phone 252 to access the main computer system via the internet 210. The user may then use the website application 264 to access the scheduling application 262 and schedule appointments, or may use the search application 266 to search for patient or inmate information, or may use the analytics application 268 to determine the pending requests and more. The user may also want to find pending requests on the analytics application 268, and then use the scheduling application 262 to effectively schedule appointments. The user may be a doctor, physician's assistant, nurse, dentist, a hygienist, a dental assistant or someone in management reviewing the progress of a facility or the individual doctors, nurses, dentists and hygienists in the facility.

Figure 3:
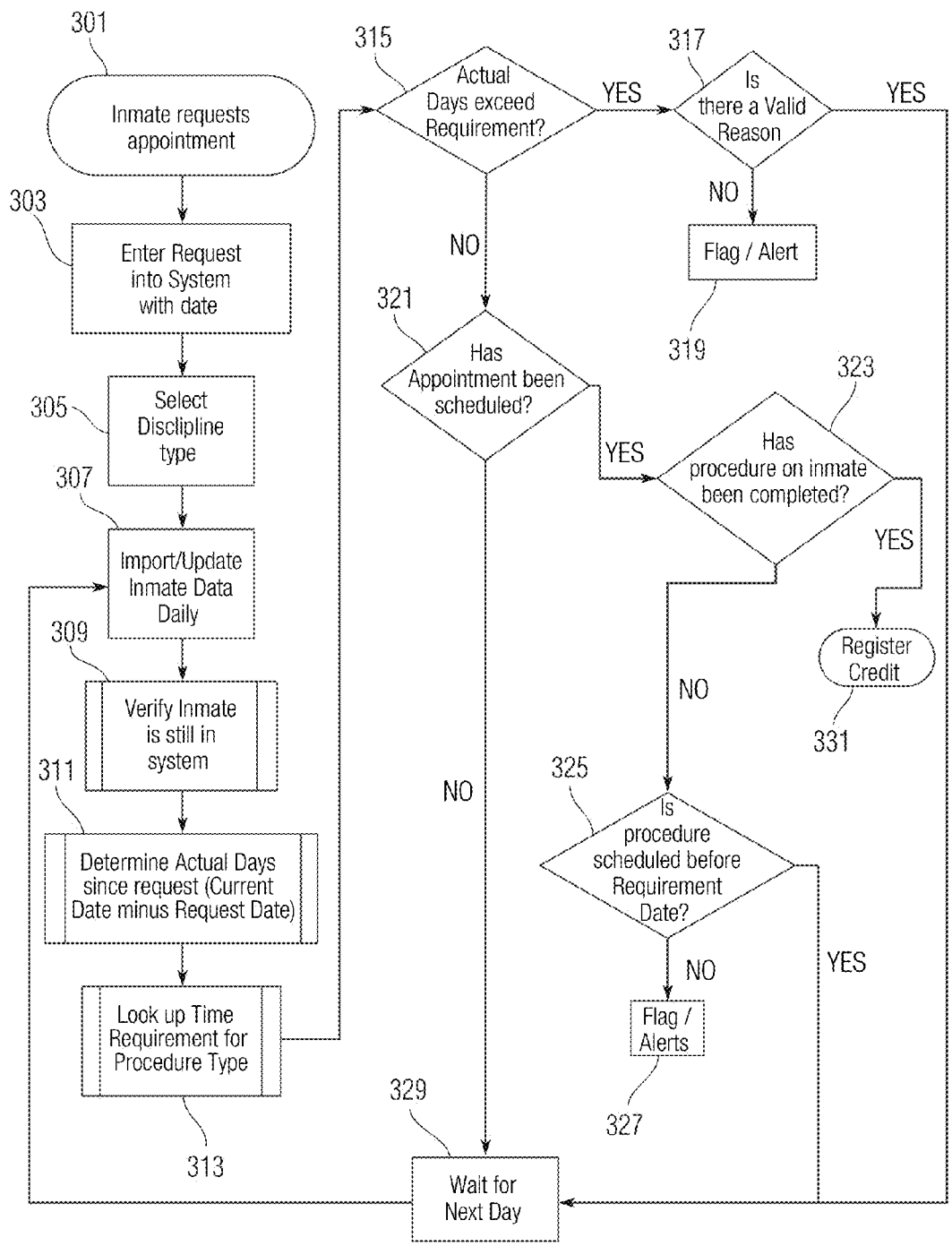
FIG. 3 illustrates a scheduling and alerting method in accordance with an exemplary aspect of the present invention.

FIG. 3 depicts the workflow method in accordance with an exemplary aspect of the present invention, and will be described in terms of a number of steps taken by the user and the system 130 described in FIG. 1.

The workflow method starts at a point in time when an inmate requests a dental appointment 301. The inmate's information is already in the system as all inmate data is downloaded daily including all transfers, new inmates, and released inmates. The user then transfers the inmate's information from the patient management display to the request management display, and assigns the Request Date 303 and discipline or procedure type 305.

Once an inmate's request is entered into the system, the system tracks the time periods specific to each discipline or procedure type which is established by applicable standards, such as those set by the state of the correction facility as well as other organizations including ACA and NCCHC. In step 307, the system imports and updates all inmate data daily. This update includes any updates related to release dates, inmate transfers, transfer dates, lockdowns, solitary and any other restrictions. In step 309, the system verifies the inmate is active in the system and has not been transferred, released, or restricted. The system then determines the actual number of days since the inmate's request was made in step 311, which is calculated as the difference between the current date and the request date. The system then determines the time requirement for the requested procedure type in step 313.

The system compares the actual number of days since the inmate's request was made against the time requirement for the inmate's requested procedure type in step 315. In the case where the actual number of days since the inmate's request exceeds the requirement date the system or user determines if there is a valid reason in step 317. The reasons might include an inmate transfer, a prison lockdown, a pending release date, the inmate is in segregation, or any other reason a system administrator might set. If there is not a valid reason, the system in step 319 will flag the inmate's request and alert the user and anyone else the system is set to notify, such as a manager or administrator, that a patient needs to be scheduled. If there is a valid excuse for the non-compliance, the system in step 329, will wait until the following day to review the data again.

In the case where the actual number of days since the inmate's request does not exceed the requirement date, the system in step 321 will check the database to determine if an appointment has been scheduled. If an appointment has not been scheduled, the system in step 329 will wait until the following day to review the data. If an appointment has been scheduled, the system in step 323 will determine whether the scheduled procedure on the inmate has been completed. In the case where the procedure has been completed, the system in step 331 will register the credit. In the case where the scheduled procedure has not been completed, the system determines whether the procedure is scheduled before the requirement date. In the event the procedure is scheduled after the requirement date, the system in step 327 will alert the user. If the procedure is scheduled before the Requirement Date, the system in step 329 will wait for the next day or processing action.

By way of example, when an administrative user receives an inmate request (step 301), the user will transfer the inmate's information in the patient management display to the request management display (step 303) and will assign a date and discipline type (step 305). In addition to the entered request, the system automatically imports and updates the inmate database on a daily basis (Step 307) finding all new transfers in and out of the system including transfers with pending requests scheduled appointments. The system then verifies if the requesting inmate's information is still in the system (step 309). The system will also determine the date of the inmate's request (step 311), and compare it against the Requirement Date (step 313). Based on the system's analysis, it will alert (step 319 and step 327) the administrative user if the number of days the inmate has been waiting exceeds the Requirement Date and/or if the procedure has been scheduled after the Requirement Date. However, if the Actual Days does not exceed the Requirement Date and no appointment has been scheduled for the transferred inmate, the system will wait until the next day (step 329) before reanalyzing the inmate's request. Alternatively, if the procedure on the inmate has been completed, the user updates the system and the system will register the credit (step 331).

Further, when an inmate transfers from one facility to another (i.e. from Facility A to Facility B), the system will automatically import into the new facility's system database any dental treatment requests by the inmate or requests that are scheduled at their previous facility (step 307). Regardless of the fact that the inmate has transferred facilities, his Request Date remains the date that he made the request at his old facility. Therefore, the system will calculate the actual days since the transferred inmate made the request at his old facility, and will compare the request date against the Requirement Date. The system will alert the administrative user if the transferred inmate's actual days since the request (Lapse Time) exceed the Requirement Date. Without such a system in place, correctional facilities using a paper and pencil process or an outdated system would require the transferred inmate to start over with a new request and his previous request would be lost.

Although the system can be used for all health, mental health, pharmaceutical care, and dental practices the system is particularly useful for dental practice management in correctional facilities. Therefore, much of the following description and figures will focus on the system as applied to dental management although the system is just as useful and applicable to health and mental health applications. Therefore, when the description refers to a dental procedure it should be assumed that this could also be a pharmaceutical, health, or mental health procedure. Further, when the description refers to a dentist, hygienist, or dental assistant it should be inferred that this also applies to doctors, physician assistants, pharmacists, nurses, and psychiatrists.

Figure 4A:
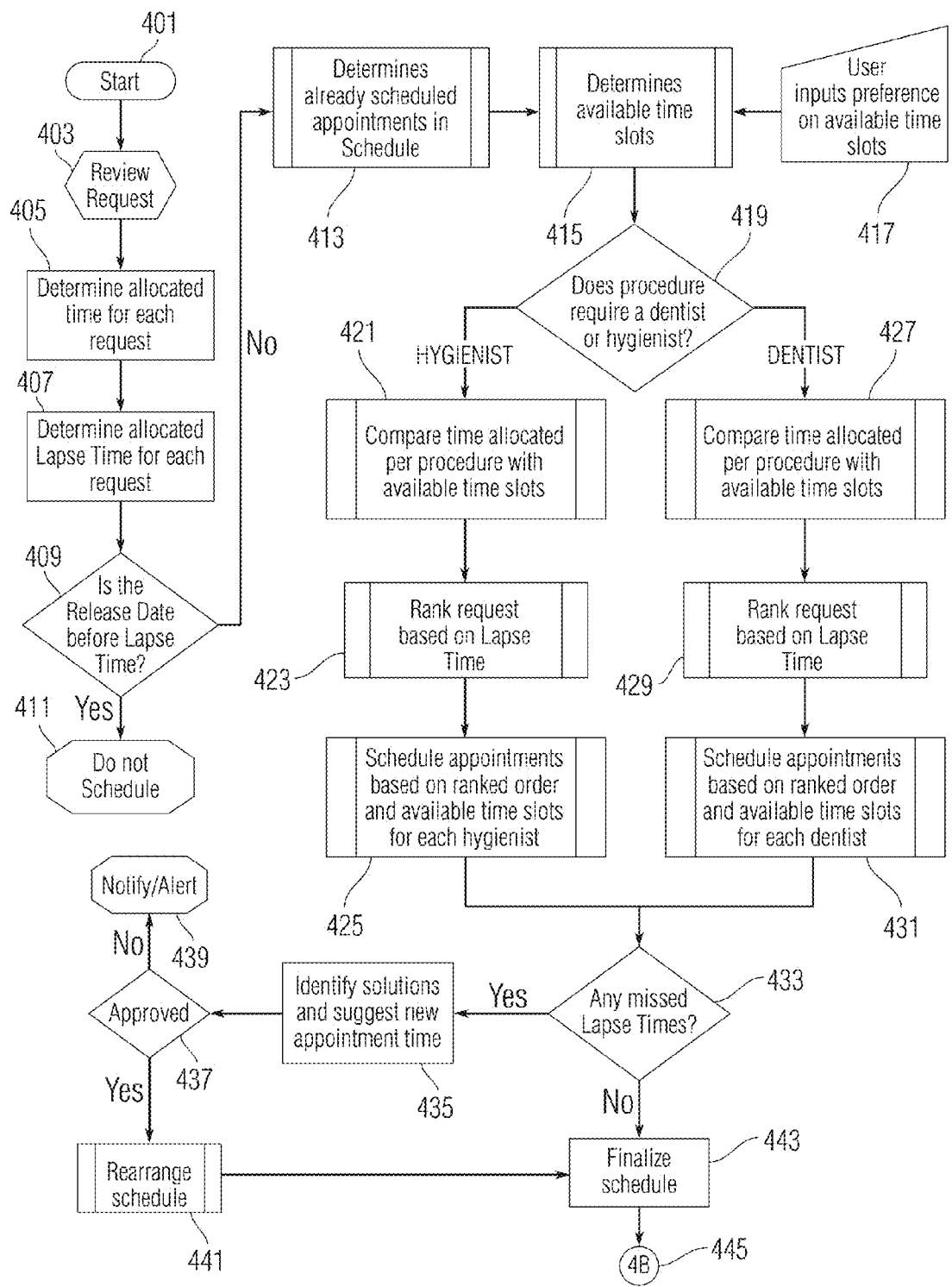
FIG. 4A illustrates the workflow method in accordance with a secondary embodiment of the present invention.
Figure 4B:
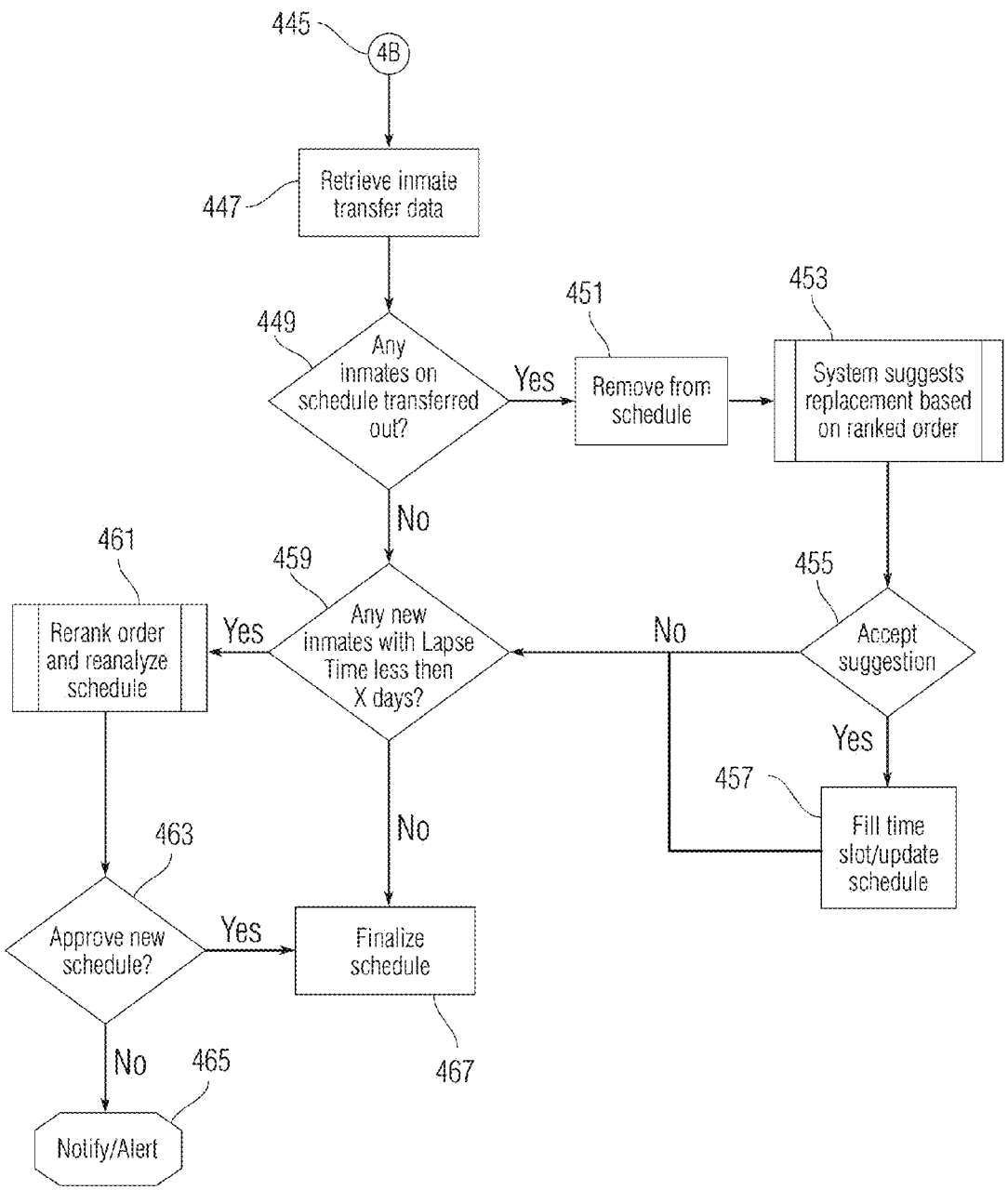
FIG. 4B illustrates additional aspects of the workflow method in FIG. 4A in accordance with a secondary embodiment of the present invention.

Although the scheduling of inmate patients will be described in more detail with regards to FIG. 8, it is important to note that the system of the present invention in its standard embodiment is ideally suited for manually scheduling inmates for their health or dental needs. The system enables the user, such as a dentist, to manually move patients (or the information of patients) from Request Management onto the schedule of a given dentist or hygienist. The user can move groups of patients over at a time or remove groups of inmates/patients from the schedule. However, and in addition to the manual scheduling, the system provides various analytics and functionality to improve the manual scheduling. As depicted in FIG. 4, an automatic scheduling and alerting method in accordance with an exemplary aspect of a second embodiment of the present invention is described in terms of a number of steps or methods performed by the system. These steps are performed by various applications or software programs running on the one or more serves 132 depicted in FIG. 1.

The system starts by reviewing all the procedure requests 403 that have not been scheduled. The requests, when entered into the system, identify the procedure type which, as depicted in FIGS. 6-19 or as described herein, include: cleanings, emergency procedures, extractions, fillings, prosthetics, scalings, restorations, intakes, endodontics, sick calls, preventative, oral surgery, and diagnostic. The system then determines the estimated amount of time each requested procedure requires 405 and the Lapse Time for each request 407. The estimated time may be a value entered by as administrative user, dentist, or hygienist based on their knowledge or may be an estimated time based on historical data of similar procedures. The estimated time may be tailored to each dentist or hygienist. By way of example, an inmate patient makes a request for a tooth extraction. The system reviews the inmate's request, and determines the estimated amount of time it takes for a tooth extraction procedure and the date the procedure must be completed by.

In step 409, the system compares the Release Date of the patient with the Lapse Time of the requested procedure. If the patient's Release Date is before the Lapse Time, the system will not schedule the patient's request In the case where the patient's Release Date is not before the Lapse Time, the system determines the appointments already scheduled in each of the dentists' and hygienists' schedules 413. Users may also input additional unavailable time slots, such as breaks or processing time, into the schedule 417. Based on the appointments already scheduled and the users' inputted data, the system determines all the available time slots of each dentist and hygienist 415.

In step 419, the system determines whether the requested procedure requires a dentist or hygienist. In the case where the request requires a hygienist, the system compares the time allocated for each procedure or the time set by the user for each procedure with the available time slots 421. The system then ranks each of the requests based on their Lapse Time 423. Once the requests are ranked, the system efficiently schedules appointments based on the ranked order and available time slots for each hygienist 425. The process is repeated for the case where the request requires a dentist. The system compares the time allocated for each procedure with the available time slots 427. The system then ranks each of the requests starting with the earliest Lapse Time 429. Once the requests are ranked, the system efficiently schedules appointments based on the ranked order and available time slots for each dentist 431.

By way of example, if one inmate needs a tooth extraction while another inmate needs a filling, the system will first determine the amount of time allocated for an extraction and a filling. The system then determines which procedure has a shorter Lapse Time. If the Lapse Time for the extraction is closer to exceeding the requirement than the Lapse Time for the filling, the system will rank the extraction before the filling, and will schedule the extraction procedure before scheduling the filling procedure.

Once all the requests have been scheduled, the system determines if there are any appointments scheduled after their respective allowable Lapse Times 433. In the case where there are no missed Lapse Times, the system will finalize the schedule 443.

However, if there are requests still pending which will exceed the maximum Lapse Time within the schedule period, the system will attempt to identify a solution, and will suggest a new schedule or appointment time 435. The suggested schedule may request appointments outside of the normal schedule such as through overtime or additional days. The user is then prompted to approve the suggested solution 437. If the user approves the suggested solution, the system will rearrange the schedule 441 and finalize the schedule 443. If the user does not approve, the system will create a notification and alert the user or others identified in the system to be notified of the potential for a missed Lapse Time 439.

It is important to note that the identified solutions by the system in step 435 may have various parameters fixed by the administrative user. For example, the user may set parameters in the system such as the maximum number of hours in a day or week, or the number of days before the system can suggest a new solution. Thus, users can specify that suggested solutions only impact the schedule the following week as an example. Further, that the system can be set to not over schedule dentists and hygienists and exceed a standard hours per day or week without notification and approval. By way of example, the system may determine that in order to meet the allowable Lapse Times, a particular dentist must work overtime. The system identifies this solution and has the ability to prompt both the dentist and a managerial user or supervisor to approve the overtime prior to scheduling.

The second embodiment of the present invention also accounts for inmates transferring in and out of the facility. Once a schedule is finalized the schedule is only changed under specific circumstances. One such circumstance relates to transferred inmates. As previously discussed and seen in step 447, the system automatically retrieves and analyzes inmate transfer data on a daily basis.

In step 449, the system determines whether any inmates with scheduled appointments have transferred out of the facility. If any of these inmates have transferred out of the facility, the system will remove them from the schedule 451, and will suggest a replacement 453 based on the ranked order and procedure type with the allocated time slot as previously described in conjunction with steps 421, 423, 429. The system then prompts the administrative user to accept the suggestion 455. If the administrative user accepts the suggestion, the system will fill the slot and update the schedule 457. If the administrative user does not accept the suggestion, the system will not fill the slot. Further, the system transfers the inmate's request to his new facility and seeks to insert his appointment into the new facility's schedule based on the same methodology.

The system also reviews the inmate transfer data, and determines whether any inmates have transferred into or out of the facility with pending procedure requests. Any requests made by transferred inmates at their old facility will automatically transfer to their new facility maintaining their original request date. As previously mentioned, current department of correction facilities do not have any system in place which allows requests from one facility to transfer to another facility while maintaining their status. However, the new facility will still have to abide by the Lapse Times of the initial request. As a result, the present invention provides a system which in step 459 determines whether the respective Lapse Times of these transferred requests are less than X days. The number of X days is set or determined by the user and is typically tied to the number of days the automatic scheduling process is set to schedule. Thus, the system can identify any transfers with Lapse Times prior to the next scheduling so that the users can determine if they can schedule the procedure in the already fixed schedule.

By way of example, the administrative user may choose to run the scheduling system every Monday scheduling for the following week. Thus, the user knows the automatic scheduling process will pick up the newly transferred inmate if the Lapse Time falls before Monday, which is the next time the scheduling system is set to run.

In a case where the Lapse Times occur before the X date, or the next time the schedule is set to run, the system will re-rank the order of Lapse Times as described in step 423, 429, and reanalyze the schedule 461. The system then prompts the administrative user for approval of the new schedule 463. If the administrative user does not approve, the system will create a notification and alert the user of the missed Lapse Times 465. If the administrative user does approve the new schedule, the system will finalize the schedule in step 467.

In the case where the Lapse Time of a newly transferred inmate occurs after the X date, or the next time the schedule is set to run, the system ignores the transferred inmate request until the next scheduled appoint run and finalizes the schedule in step 467.

By way of example, when an inmate requests dental treatment, the user will create this request in the system. The system will analyze and schedule the pending request during its next cycle. The frequency that the system runs is set by the facility. Based on the time allocated for each request, the Lapse Time for each request, the Release Date of the inmate, and the dentist's or hygienist's schedule, the user may manually schedule or have the system automatically schedule appointments for each of the pending requests. If any of the requested procedures are scheduled cannot be scheduled before their Lapse Time, the system will alert the administrative user and suggest a solution. The user may choose to accept the systems suggested solution and, if accepted, the system will automatically rearrange the schedule.

As an additional example, when an inmate has transferred into the facility, the system will automatically retrieve this data into the system's database and is available within the patient management application. Further, if the inmate had a request or a scheduled appointment at their old facility the request would automatically go into the Request Management application. If the inmate's Lapse Time occurs before the system's next scheduling cycle, the system will automatically rearrange the schedule and prompt the administrative user for approval of the revised schedule. During the rescheduling analysis, the system looks for procedures with less immediate Lapse Times which could be rescheduled later while trying to schedule in the transferred procedure with a more immediate Lapse Time. Further, when an inmate transfers out of the facility, the system automatically removes any appointments for that transferred inmate from the schedule. The system will then automatically determine one or more replacement appointments and prompts the administrative user for approval. If the administrative user chooses to accept the replacement, the system will fill the time slot with the replacement and update the schedule.

In addition to the scheduling function, the system may also provide users of the system and other related parties, such as administrative users, dentists, hygienists, and prison guards, with a daily and weekly scheduling report. In the event changes are made to the fixed schedule, the system may notify these users and related parties of any adjustments made to the schedule, and may provide them with updated scheduling reports.

By way of example, the scheduling system may pick up a newly transferred inmate who requires an appointment to be scheduled immediately. As a result, the system will rearrange the already fixed schedule to accommodate the transferred inmate. Once the administrative user approves the rearranged scheduled, the system will automatically send notifications to users of the systems and other related parties, such as administrative users, dentists, hygienists, and prison guards, of the adjustment to the fixed schedule, and will provide these parties with an updated scheduling report.

As will be described in more detail in conjunction with FIGS. 5-19, the user interacts with the software through the various graphic user interface screens of the system. FIGS. 5-19 depicts one embodiment of the present invention.

Figure 5:
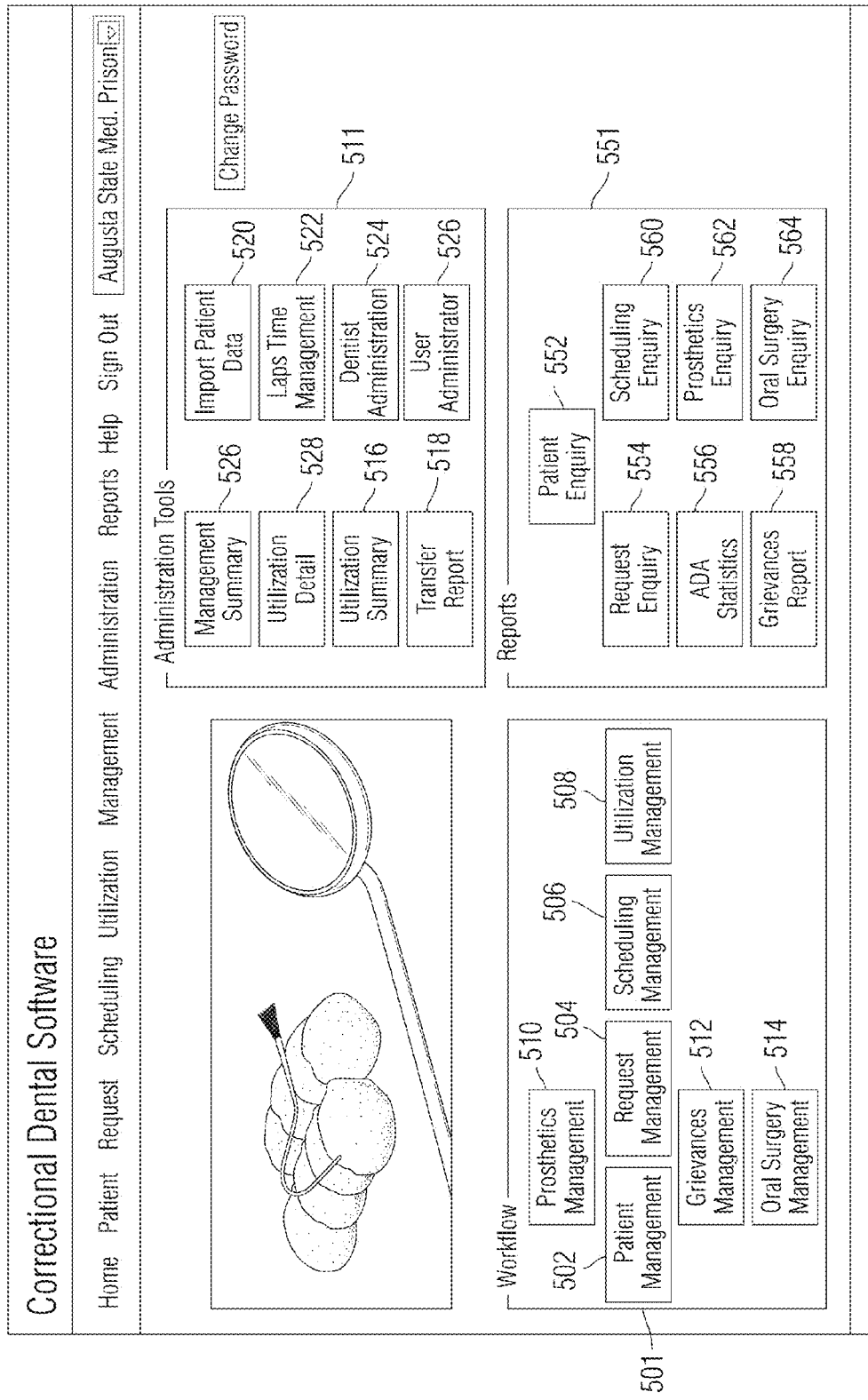
FIG. 5 illustrates a graphical user interface of the main page according to an aspect of the present invention.

FIG. 5 depicts a graphical user interface of the homepage of the Correctional Dental Software website. Users may access the system 130 as described in FIG. 1 through this homepage 500. On this homepage screen 500, users can navigate to specific applications of the system using navigational buttons 502, 504, 506, 508, 510, 512, 514, 516, 518, 520, 522, 524, 526, 528, 552, 554, 556, 558, 560, 562, 564. By clicking on a specified navigation button, the user is led to an individual display for that specified navigational button. The navigational buttons are divided into three groupings: Workflow 501, Administrative Tools 511, and Reports 551.

The Workflow 501 grouping consists of the following navigational buttons: Patient Management 502, Request Management 504, Scheduling Management 506, Utilization Management 508, Prosthetic Management 510, Grievances Management 512, and Oral Surgery Management 514. The individual displays that correlate with each specified navigational button listed in the Workflow 501 group are further described in FIGS. 6-12.

The Administrative Tools 511 grouping consists of the following navigational buttons: Management Summary 526, Utilization Detail 528, Utilization Summary 516, Transfer Report 518, Import Patient Data 520, Lapse Time Management 522, Dentist Administration 524, and User Administration 526. The individual displays that correlate with each specified navigational button listed in the Administrative Tool 511 group are further described in FIGS. 13-19.

The Reports 551 grouping consists of the following navigation buttons: Patient Enquiry 552, Request Enquiry 554, ADA Statistics 556, Grievances Report 558, Scheduling Enquiry 560, Prosthetics Enquiry 562, and Oral Surgery Report 564.

A Patient Enquiry Report is utilized to view the dental treatment history of any patient. After the user clicks on the Patient Enquiry navigational button 552 and enters a patient identification number or name, the will system provide the user with a history of treatment to that specified patient along with dates and procedures performed.

A Request Enquiry Report is utilized to view the dental requests submitted during a specified time frame. After the user clicks on the Request Entry navigational button 554 and enters a time frame in the Request Date field, the system will provide the user a Request Entry Report. The user may also select to sort the report by status or specialty/procedure type.

An ADA Statistics Report is utilized to generate utilization reports based on services rendered by ADA codes for a specific time period. After the user clicks on the ADA Statistics navigational button 556 and enters a time frame in the Request Date field, the system will provide the user an ADA Statistics Report and report of all procedures performed.

A Grievance Report is utilized to track and view the status of all grievances. After a user clicks on the Grievance Report navigational button 558 and enters a time frame, the system will provide the user with a Grievance Report. The user may also select to sort the report by status or level of the grievance.

A Scheduling Enquiry is utilized to search and view/print schedules for a specific day or a range of dates by specialty/procedure type or dentist/hygienist (past and future). After the user clicks on the Scheduling Enquiry navigational button 560 and enters a time frame, the system will provide the user with a Scheduling Enquiry Report. The user may also select to sort the report by specialty/procedure type or dentist. These reports can also be exported into an excel or similar spreadsheet document which can be emailed to security so they know which inmates to bring over to dental.

A Prosthetics Enquiry Report is utilized to view the status of ongoing prosthetic cases. After a user clicks on the Prosthetics Enquiry navigational button 562 and enters a time frame, the system will provide the user with a Prosthetics Enquiry Report. The user may also select to sort the report by case status.

An Oral Surgery Enquiry Report is utilized to view the status of oral surgery cases referred out. After the user clicks on the Oral Surgery Report 564 navigational button and enters a time frame, the system will provide the user with an Oral Surgery Enquiry Report. The user may also select to sort the report by "Status."

Figure 6:
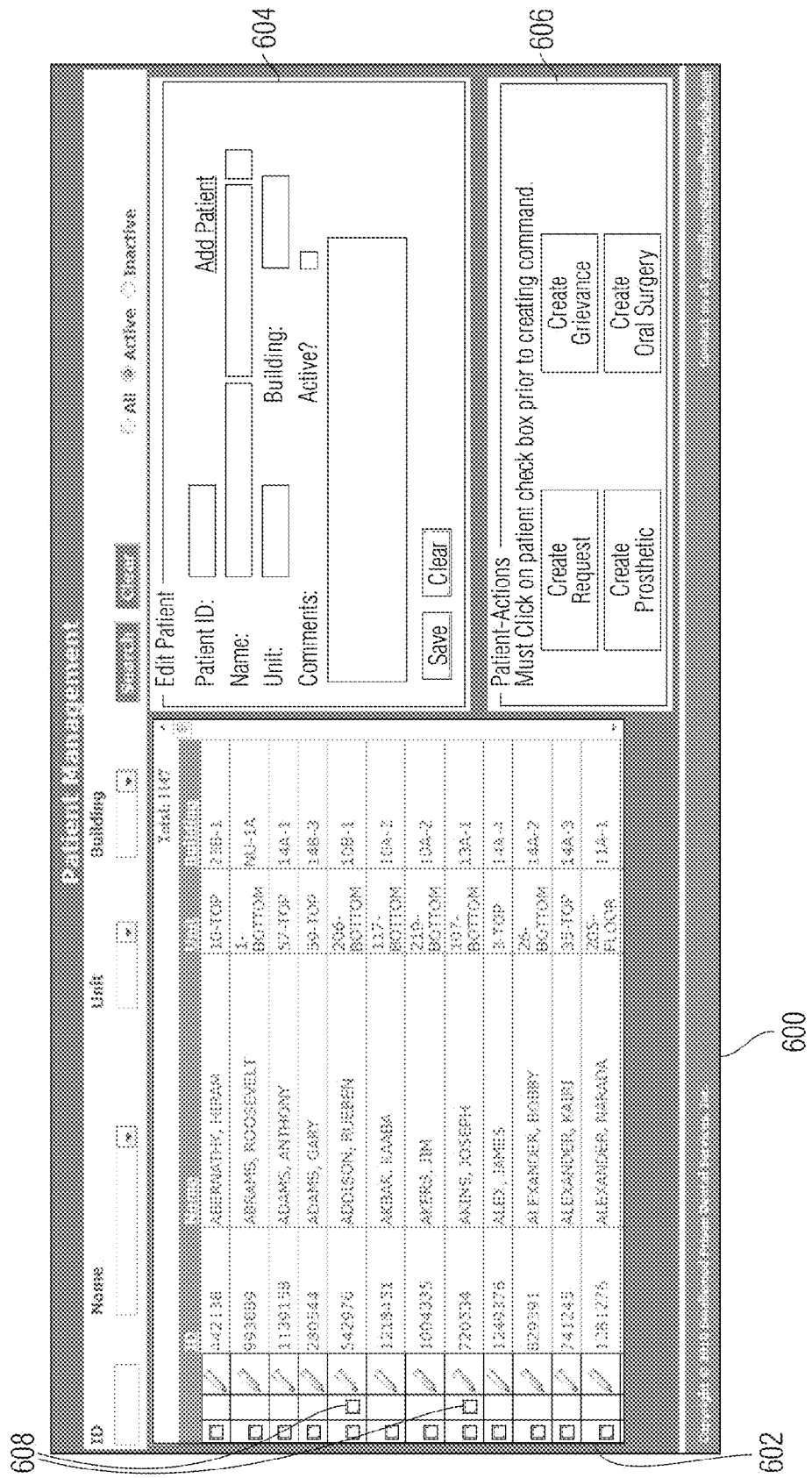
FIG. 6 illustrates a graphical user interface of the Patient Management display in accordance with the present invention.

FIG. 6 depicts a graphical user interface of the Patient Management display 600 including patient identification numbers, names, and unit and building information. The Patient Management display 600 is the database that maintains all patient information. If the facility has an electronic bed log, the data can be transferred into the system's database. Data is electronically transferred from the facility into the system on a daily basis to ensure the system knows which inmates are present and which are not. Importing data from the electronic bed log is further described in FIG. 17.

When a request for dental treatment is made, the user may enter the Patient Management display 600 through the homepage 500 as described in FIG. 5. The user may search for the respective patient information by either the patient identification number or the patient's name or scroll through the list of patient information.

The results window 602 displays the patient identification number, name, unit, and building information. The user may sort the results in window 602 by the patient identification number, name, unit number or building. The user may also click on the "pencil" located next to each patient's name in the results window 602 to reveal more detailed information and notes regarding the respective patient.

The patient data is displayed on the right-hand side of the screen 604 when the user clicks on the pencil icon. A second icon 608 may also be displayed between the checkbox icon and the pencil icon. This second icon 608 informs the user that this inmate already has a request that he is waiting to be treated for. By clicking this second icon 608, the user can view the requests that the inmate already has pending to avoid putting in a second request. This is particularly useful as inmates are known to submit repeated requests for the same problem or procedure.

The user may create a Dental Request by checking the box next to the appropriate patient's name found within the search results 602, and then clicking the Create a Request navigational button located in the Patient Actions section 606. Clicking on the Create a Request navigational button will transfer the patient information into the Request Management display as described further later with reference to FIG. 7.

The user may also track specialized requests, such as Oral Surgery, Grievances, and ongoing Prosthetic cases, by clicking the navigational buttons located in the Patient Actions section 606. Clicking on each of these navigational buttons will transfer the user to the respective displays with the selected inmate's or patients information transferred and further described herein in conjunction with FIGS. 10-12.

The user may also edit or add patient information by using the Edit Patient section 604. The user may also include comments for each patient and those comments are transferred to all reports. The "active" checkbox in the Edit Patient section 604 is used to identify whether the patients have been transferred in or out of the correctional facility.

By way of example, if a patient's information is not yet in the system, the administrative user may use the Patient Management display 600 to enter the patient's information into the database and also create a dental treatment request or create specialized requests.

Figure 7:
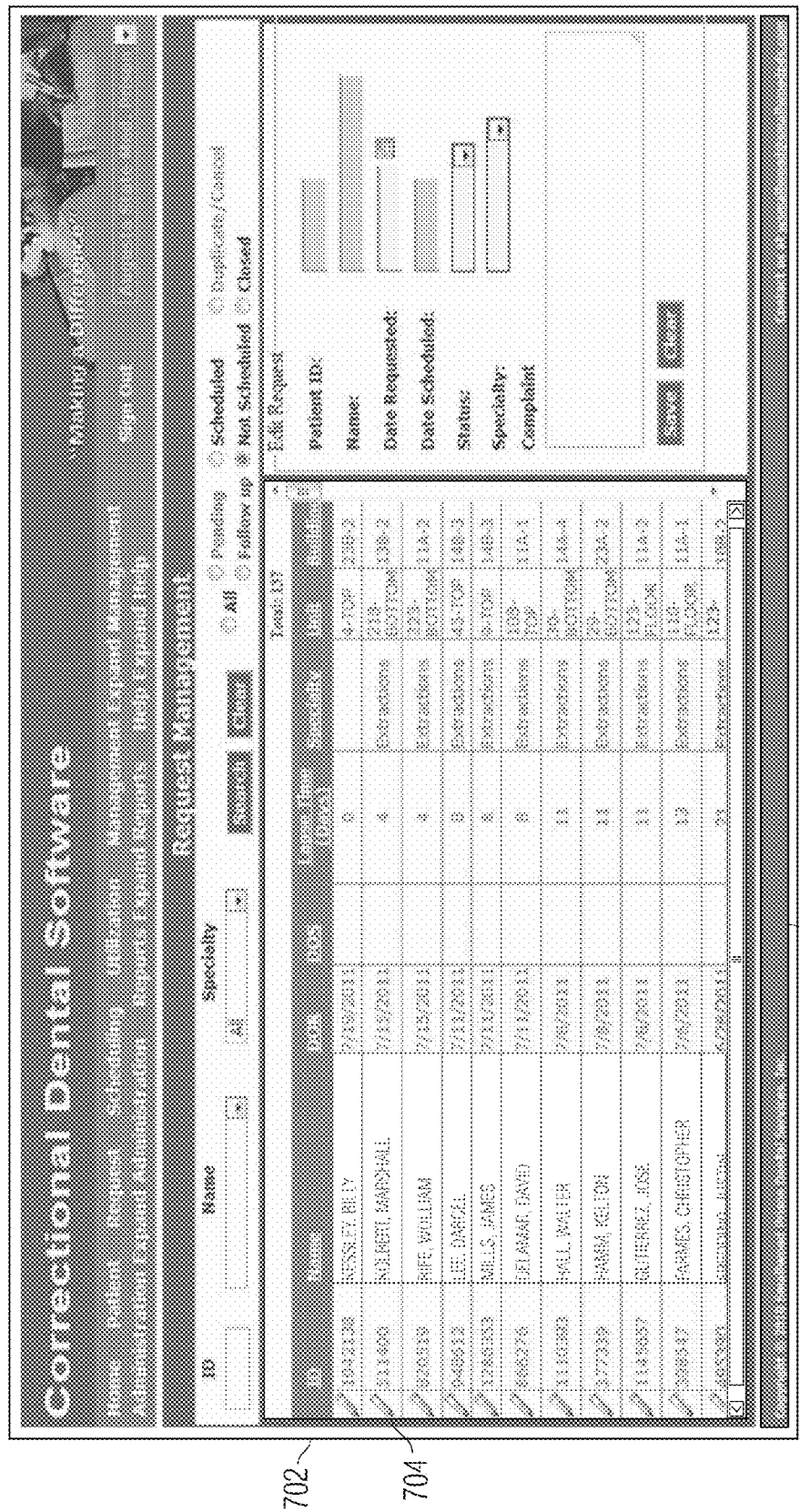
FIG. 7 illustrates a graphical user interface of the Request Management display in accordance with the present invention.

FIG. 7 depicts a graphical user interface of the Request Management display 700 including patient identification numbers, names, dates of request, dates of scheduling, lapse times, specialty, and unit and building information along with an area for editing requests. A user may enter the Request Management display 700 through the Request Management navigational button 504 on the homepage 500 as described in FIG. 5 or through the Patient Management display 600 as described in FIG. 6.

Patients who have submitted a dental treatment request are listed on the left-hand side of the screen 702. The requests with any issues or errors will appear first on the left-hand side of the screen 702. Such issues or errors could be missing information such as the lack of a specified specialty. After such requests are listed, the most recent requests will appear next on the left-hand side of the screen 702. The following information will appear for each patient: patient identification number, name, date of request (DOR), date of scheduling (DOS), the lapse time (time difference in days between DOR to current day), specialty requested, and unit and building information. The user may search for patient information by either the patient identification number or the patient's name. The user may also sort the patient information by the status of their request, DOR, DOS, lapse time, specialty, unit, and building.

In order to enter or edit a request, the user must click on the "pencil" 704 located next to the patient's name. By clicking on the "pencil," the patient's information and the date of request will automatically populate in the Edit Request section, and the user may then enter a dental treatment request. To enter a dental treatment request, the user must enter the status, specialty, and the complaint. By clicking "Save," the user will automatically be transferred to the Schedule Management display which is described further in FIG. 8.

Because it is not uncommon for inmates to send multiple requests for the same problem, the system automatically checks already pending requests for the same inmate. Therefore, when the user clicks "Save" after creating a request, the system checks to see if the inmate already has a request in the Request Management for the same specialty and dentistry procedure. If the inmate already has a request for the same specialty or dentistry procedure, the system will prompt the user to either (1) Continue or (2) Mark as Duplicate. If the user clicks Continue, the system will accept the request and add it as a new request. This might be useful if the patient needs numerous extractions which will take more than one visit. Alternatively, if the user selects Mark as Duplicate the system will ignore or delete the new request. This novel feature prevents an overload of requests and helps maximize the efficiencies of maintaining the total inmate population.

By way of example, once the patient's information is in the system, an administrative user may use the Request Management display 700 to track and report all dental requests, and to create a request in the system. Once a request is made in the system, the administrative user will be redirected to the scheduling screen.

Figure 8:
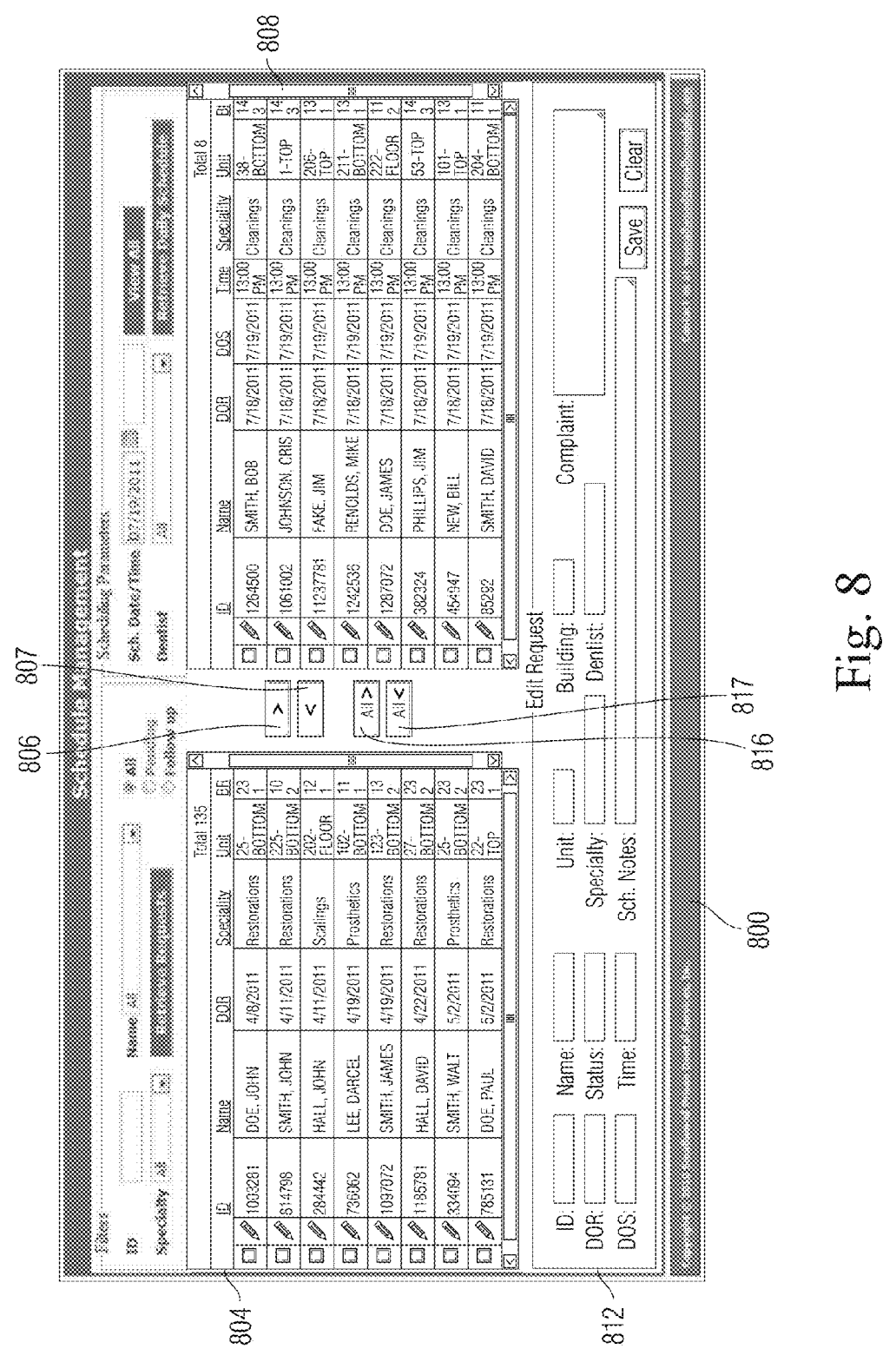

FIG. 8 depicts a graphical user interface of the Schedule Management display 800 including patient identification numbers, names, dates of requisition, specialty, and unit and building information along with scheduling parameters. The user may enter the Schedule Management display 800 through the homepage 500 as described in FIG. 1 or the Request Management display 700 as described in FIG. 7.

All patients that need to be scheduled are found on the left-hand side of the screen 804. The user may sort the patient information by the patient identification number, name, DOR, specialty, unit number or building. The user may also filter the patient information by fields including the specialty or procedure type, or the case status/pending/follow-up.

To schedule an appointment, the user must enter the appropriate Scheduling Parameters in the upper right hand of the Schedule Management display 800. Such parameters may include the date, time, or specified dentist or hygienists. A list of the patients who have already scheduled appointments will appear on the right-hand side of the Scheduling Management display 808 in accordance with the Schedule Parameters entered by the user.

By way of example, if the user selects a specific dentist in the Schedule Parameter section, a list of that dentist's scheduled appointments will populate on the right-hand side of the screen 808. The user may then use the arrow buttons 806, 807 to transfer the unscheduled patients on the left-hand side of the screen 804 to the right-hand side of the screen or vice-versa. To schedule an appointment, the user must move the patient from the left-hand side of the screen 804 to the right-hand side of the screen 808 using the right arrow button 806. The user may sort the patient information listed on either side of the screen 806, 808 by the patient identification number, name, date of request (DOR), specialty, unit number or building. In addition, the user may sort the already scheduled patients by date of service (DOS) and appointment time.

By clicking on the "pencil" beside a patient's name, the user will pull up the details of that respective patient on the bottom of the screen. Once the patient is scheduled, clicking on the "pencil" beside the patient's name will allow the user to edit the appointment.

By way of example, an administrative user may utilize the Schedule Management display 800 to schedule all patient requests. Once an administrative user has created a request through the Request Management display 700, he may use the Schedule Management display 800 to schedule the request, to search for already scheduled requests, to track requests that need to be scheduled, and to retrieve the daily schedules of each dentist and hygienists. The inmates which need to be scheduled are displayed in the "To Be Scheduled" window 804 and the patients already scheduled are displayed in the "Scheduled Patients" window 808.

Figure 9:
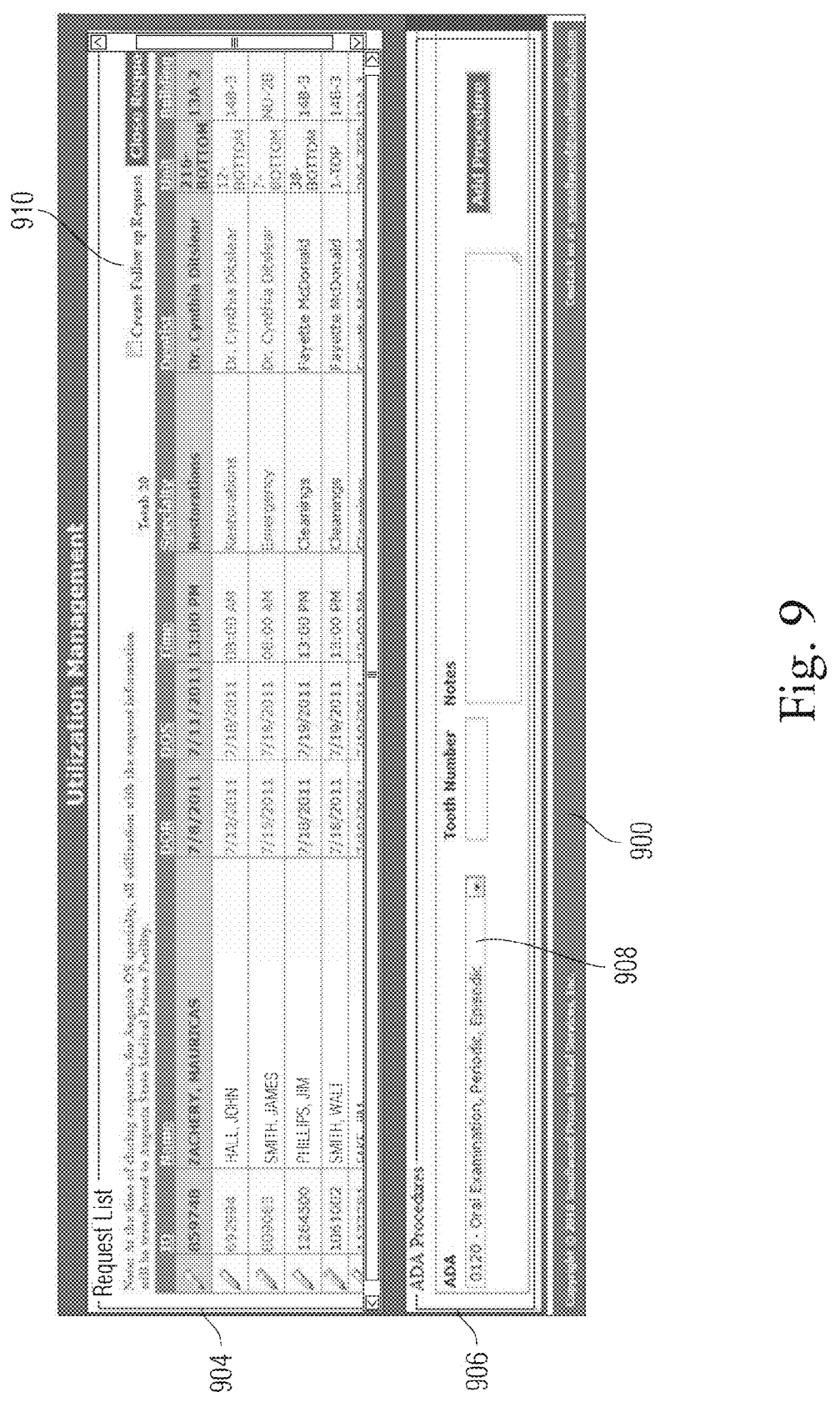

In addition, when the prison environment is in a lockdown, no patients can be treated and all the patients must be unscheduled. The all arrow buttons 816, 817 allow the user to either schedule all the patients on the left hand-side of the screen displayed in window 804 or unscheduled all patients on the right hand side of the screen displayed in window 808. When the patients are unscheduled, the inmate patient will electronically move back to the Request Management display of window 804, and the DOS will be removed awaiting for the inmates/patients to be rescheduled FIG. 9 depicts a graphical user interface of the Utilization Management display 900 including patient identification numbers, names, dates of request, dates of scheduling, times, specialty, dentist, and unit and building information along with a field for entering procedure names, numbers, and notes. The Request List 904 displays all the patients that have been scheduled and need to have utilization entered. Clicking on the "pencil" located next to the patient's name selects that patient for utilization. Once selected, the user may add or edit ADA procedures in the ADA Procedures section located on the bottom of the Utilization Management display 900.

When the user clicks on "Close Request" the request is closed out and credit for those procedures is recorded. If the user wants to close out the case and schedule another appointment, the user will click on create follow-up request. This will close out the case, provide the credit from completing the procedure, and create another request in Request Management. This saves time as compared to going back to Patient Management and transferring the patient information from Patient Management to Request Management.

By way of example, a department of correction supervisor may review the Utilization Management display 900 to ensure that all utilization is accounted for, to review the status of each dental treatment request, and to close out requests after the dental serves are provided.

Figure 10:
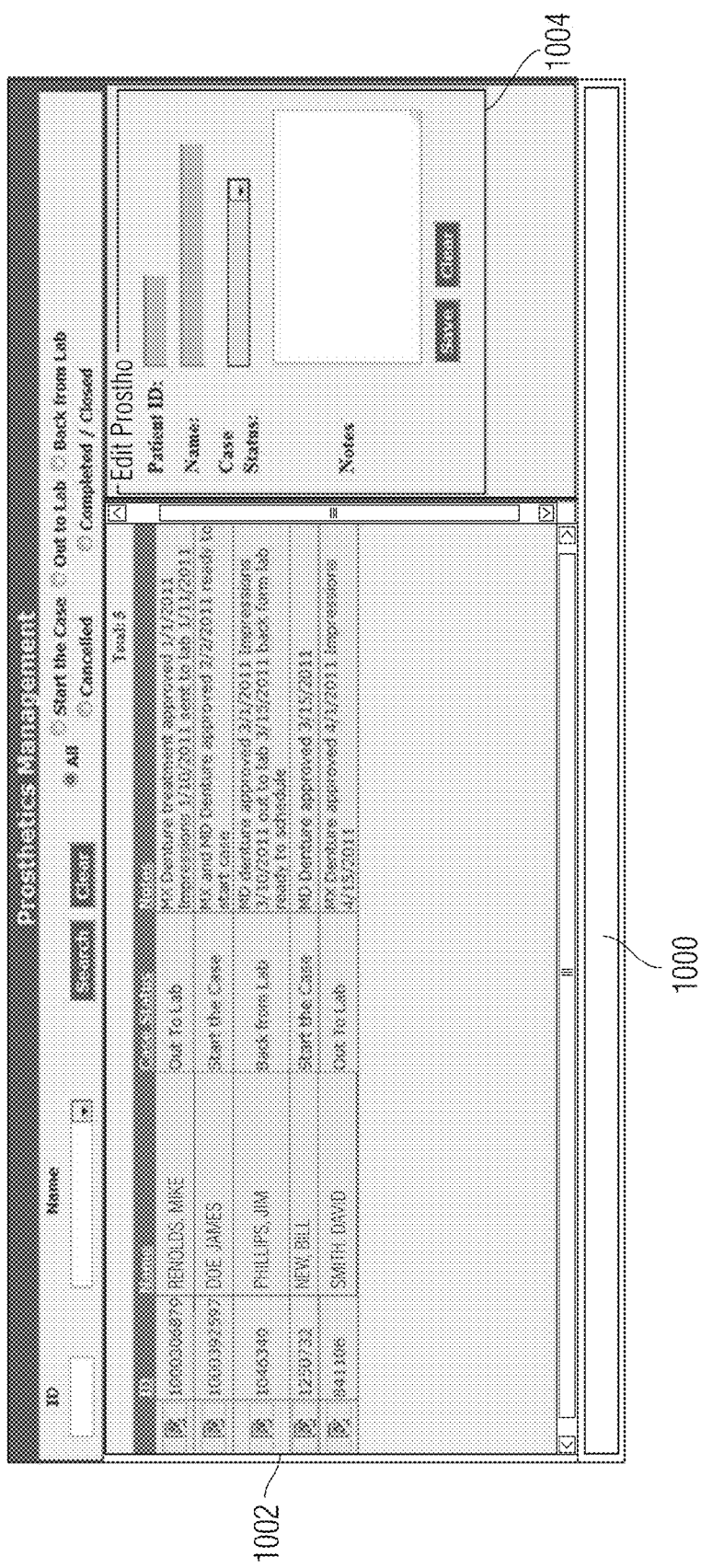
FIG. 10 illustrates a graphical user interface of the Prosthetics Management display in accordance with the present invention.

FIG. 10 depicts a graphical user interface of the Prosthetics Management display 1000 which tracks the progress of all prosthetics cases once it has been determined that the patient qualifies for a prosthetic. When a patient qualifies for a prosthetic (denture or partial), the user identifies the patient in Patient Management (window 602 of FIG. 6) and in the Patient Actions section 606, selects "Create Prosthetic." This will transfer the patient data into Prosthetics Management.

The user may enter the Prosthetic Management display 1000 through the Prosthetics Management navigational button 510 on the homepage 500 as described in FIG. 5 or the Patient Management display 600 as described in FIG. 6.

Patients who have been qualified for prosthetics are listed on the left-hand side of the screen 1002. The following information will appear for each patient: the patient identification number, patient's name, case status, and notes. The user may search for patient information by either the patient identification number or the patient's name. The user may also sort the patient information by the case status.

To edit a prosthetics request, the user must click on the "pencil" located next to the patient's name. By clicking on the "pencil," the patient's information will automatically populate on the right-hand side of the screen 1004, and the user may then edit the prosthetics request.

By way of example, an administrative user may use the Prosthetic Management display 1000 to view the prosthetics history of patients, track the status of prosthetic requests, or edit requests.

Figure 11:
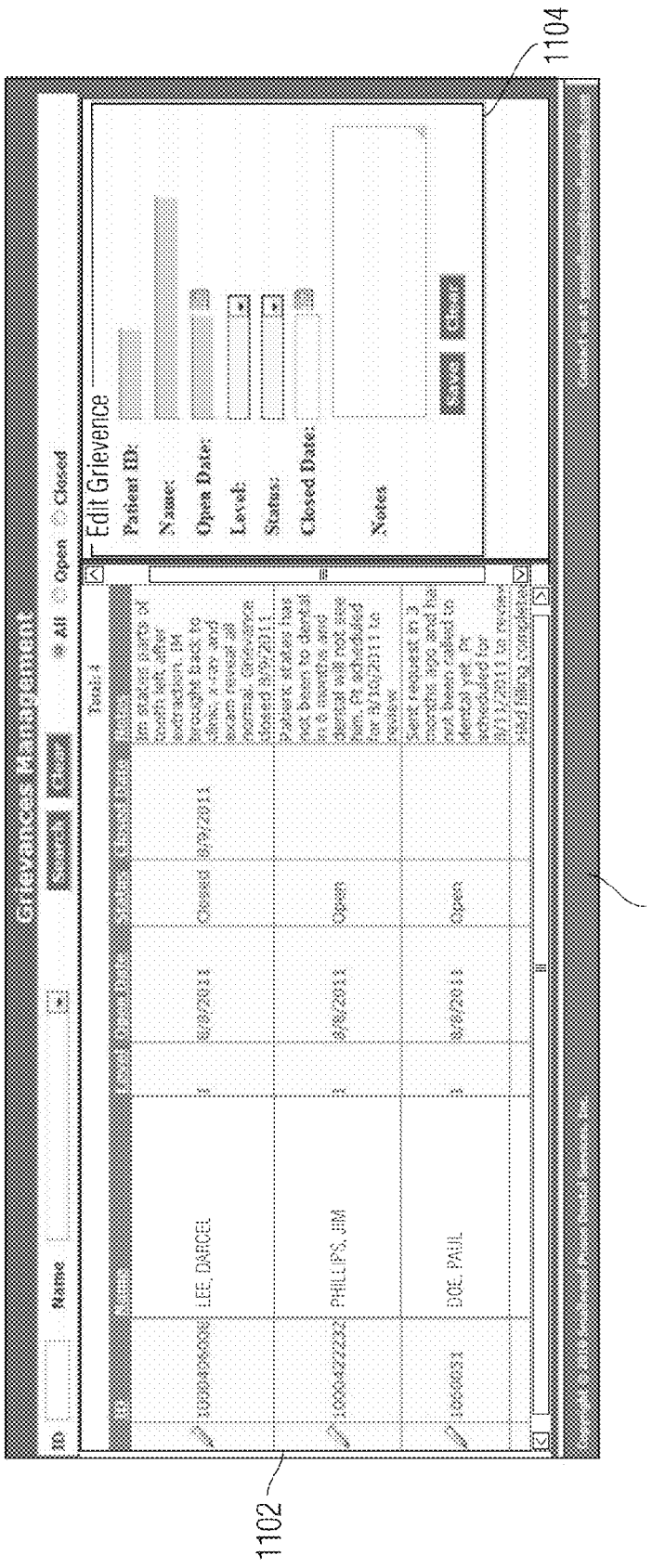
FIG. 11 illustrates a graphical user interface for the Grievances Management display in accordance with the present invention.

FIG. 11 depicts a graphical user interface of the Grievances Management display 1100 which tracks grievances. When a patient submits a grievance, the user identifies the patient in window 602 of the Patient Management screen 600 (see FIG. 6) and in the Patient Actions section 606, selects "Create Grievance." This will transfer the patient data into Grievances Management.

The user may enter the Grievances Management display 1100 through the Grievances Management navigational button 512 on the homepage 500 as described in FIG. 5 or the Patient Management display 600 as described in FIG. 6.

Patients who have filed grievances are listed on the left-hand side of the screen 1102. The following information will appear for each patient: patient identification number, patient's name, level, date grievance was entered (open date), case status, date grievance was closed (closed date), and notes. The user may search for patient information by either the patient identification number or the patient's name. The user may also sort the patient information by the status of their case, the date the case was opened or closed, and by level.

To edit a grievance request, the user must click on the "pencil" located next to the patient's name. By clicking on the "pencil," the patient's information will automatically populate on the right-hand side of the screen 1104, and the user may then edit the grievance request.

By way of example, when a grievance is received, an administrative user may use the Grievance Management display 800 to create the grievance, track the grievance, and edit the grievance by updating its status and entering notes pertaining to the grievance.

Figure 12:
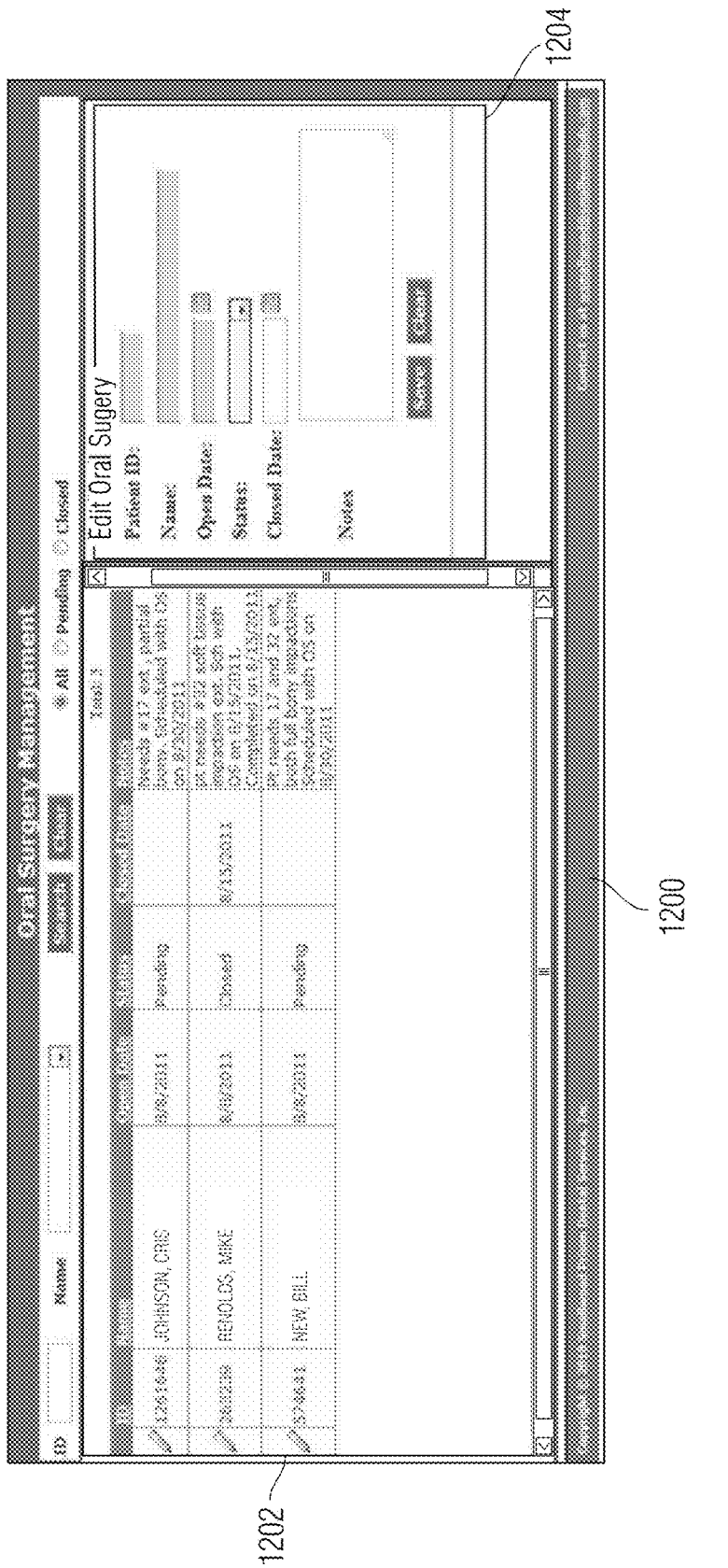
FIG. 12 illustrates a graphical user interface for the Oral Surgery Management display in accordance with the present invention.

FIG. 12 depicts a graphical user interface of the Oral Surgery Management display 1200 which tracks progress on all cases referred to an oral surgeon. When a patient qualifies for an oral surgery, the user identifies the patient in window 602 of the Patient Management screen 600 (see FIG. 6) and in the Patient Actions section 606, selects "Create Oral Surgery." This will transfer the patient data into Oral Surgery Management.

The user may enter the Oral Surgery Management display 1200 through the Oral Surgery Management navigational button 514 on the homepage 500 as described in FIG. 12 or the Patient Management display 600 as described in FIG. 6.

Patients with approved referrals to an oral surgeon are listed on the left-hand side of the screen 1202. The following information will appear for each patient: patient identification number, patient's name, date the request was made (open date), the case status, the date the request is closed (closed date), and notes. The user may search for patient information by either the patient identification number or the patient's name. The user may also sort the patient information by case status or the date the case was opened or closed.

To edit an oral surgery request, the user must click on the "pencil" located next to the patient's name. By clicking on the "pencil," the patient's information will automatically populate on the right-hand side of the screen 1204, and the user may then edit the oral surgery request.

By way of example, a user may use the Oral Surgery Management display 1200 to view the oral surgery history of patients, track the status of oral surgery requests, or edit oral surgery requests.

Figure 13:
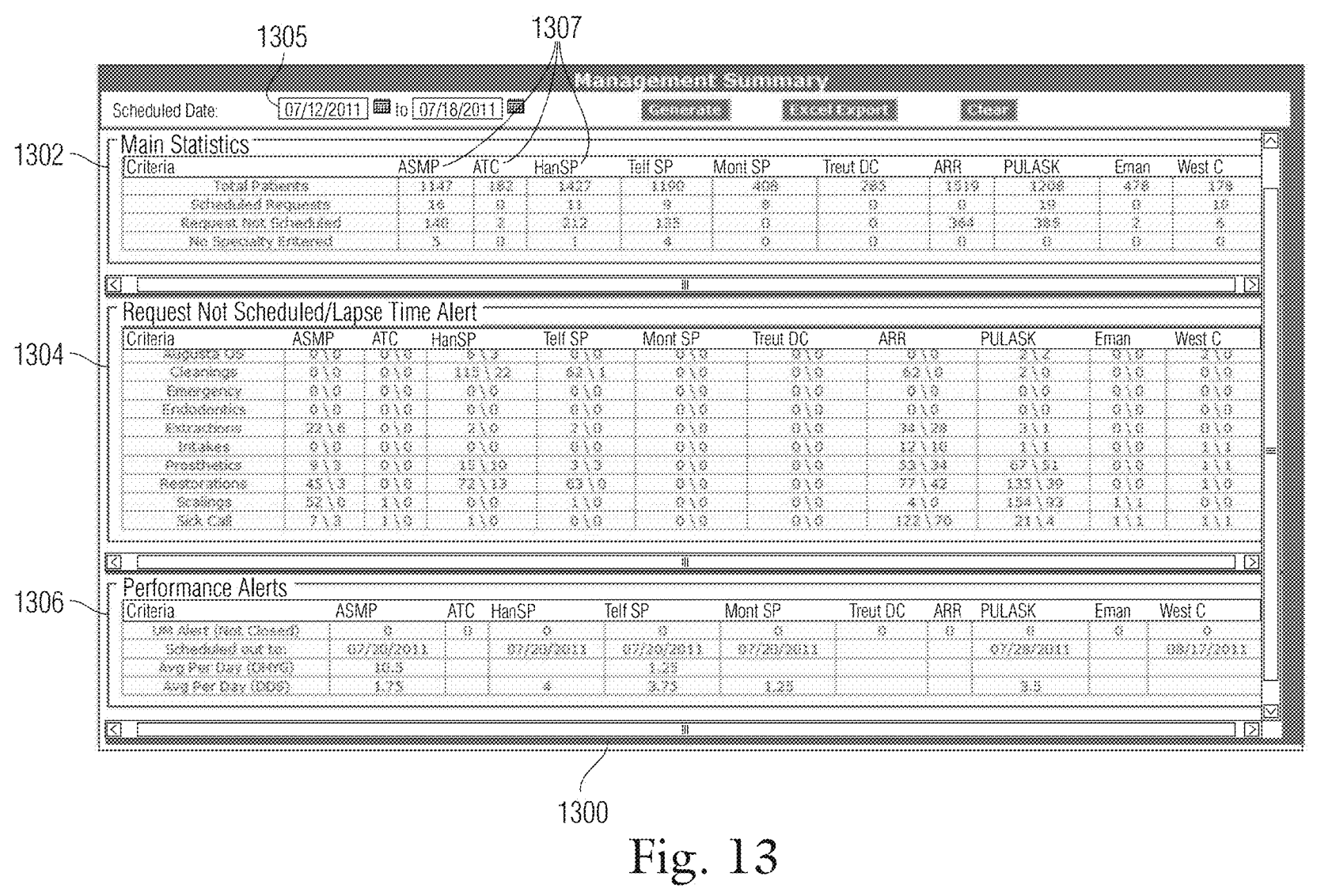

FIG. 13 depicts a graphical user interface of the Management Summary display 1300. The Management Summary display 1300 can only be viewed by "Senior Management," and not by all users. The purpose of Management Summary is to provide "Senior Management" the ability to manage multiple facilities with ease. Rather than going into each facility to view progress (or lack thereof), the Management Summary display provides a "snap shot picture" of the performance of all facilities and provides very specific key indicators to view.

A user may enter the Management Summary display 1300 through the Management Summary navigational button 526 on the homepage 500 as described in FIG. 5.

The Management Summary display 1300 includes the Main Statistics 1302, Requests Not Scheduled/Lapse Time Alert 1304, and Performance Alerts 1306. These alerts include criteria for the prison facilities 1307. The Main Statistics 1302 allows users to view criteria such as the total number of patients, scheduled requests, requests not scheduled, and requests without any specified procedure entered utilized to reduce user error. The Requests Not Scheduled/Lapse Time Alert 1304 allows users to view criteria such as the number of requests not scheduled and the number of requests flagged by the system with Lapse Time alerts. The Lapse Time alerts were previously described in conjunction with FIG. 3 where the system will alert the user of any requests and procedures that are not scheduled or completed before the required lapse times established by each individual state. The Performance Alerts 1306 allows users to view criteria on the overall performance of a facility. The performance shows the average number of patients seen per day by the dentists and hygienists in each facility. A user may also view the statistics for a specified time period 1305 and export to an excel document of the statistics generated.

By way of example, a facility supervisor may use the Management Summary display 1300 to effectively manage multiple facilities by viewing detailed activity reports for each facility. Typically, the user views and the system is set (defaults to) a view of the last thirty (30) days.

Figure 14:
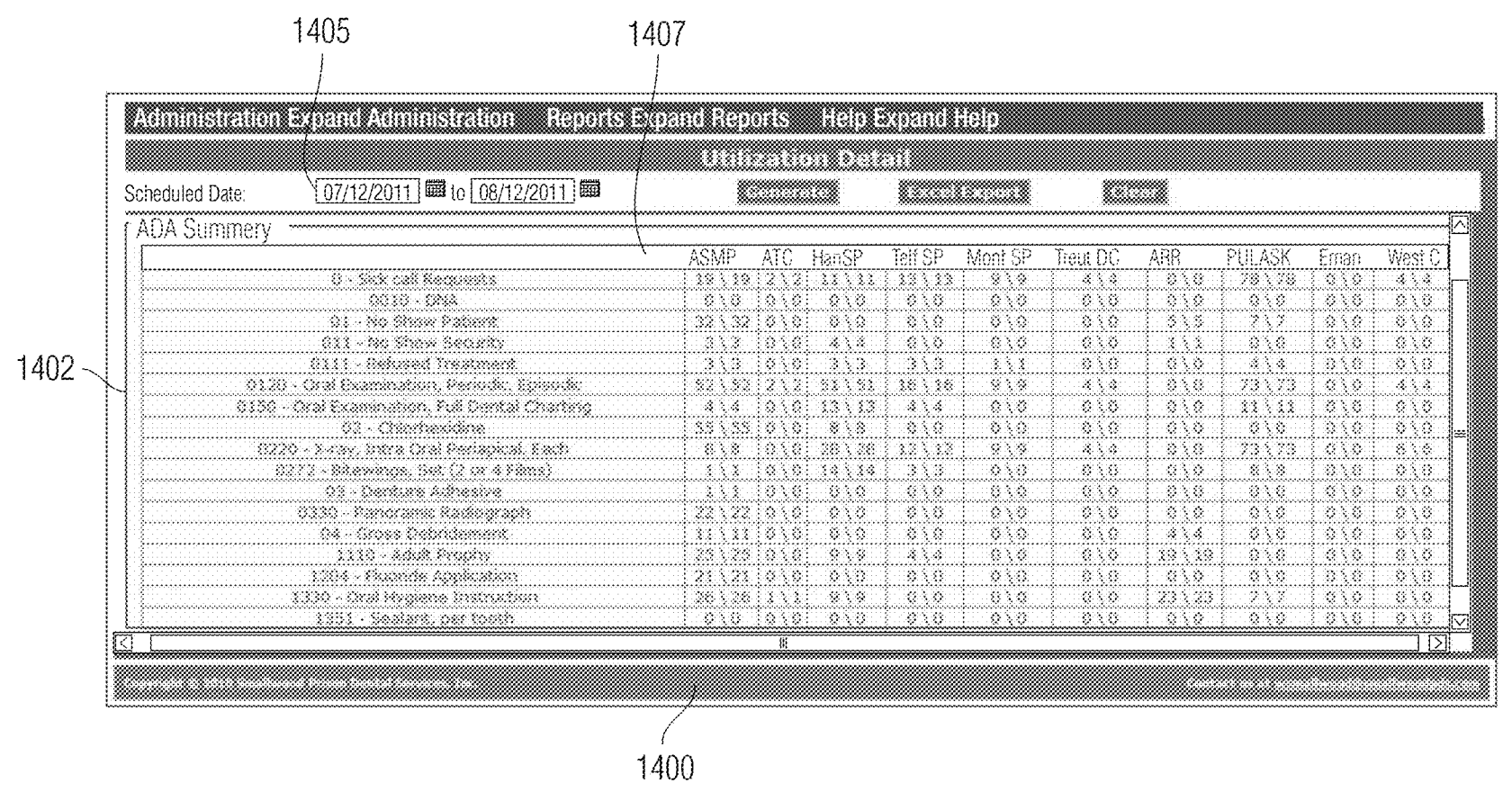

FIG. 14 depicts a graphical user interface of the Utilization Detail display 1400. A user may enter the Utilization Detail display 1400 through the Utilization Detail navigational button 528 on the homepage 500 as described in FIG. 5. The Utilization Detail display 1400 includes an ADA Summary 1402 of all facilities with coding and information for all prisons/facilities 1407. A user may view the statistics for a specified time period 1405 and export an excel document of the statistics generated.

By way of example, a Senior Management user may use the Utilization Detail display 1400 to effectively manage multiple facilities by viewing the utilization for each facility. The first number in the data displayed shows the total number of procedures performed over the date period set by the date range 1405 and the second number shows the average number of procedures over the date period set by the date range 1405 for each procedure displayed in window 1402.

Figure 15:
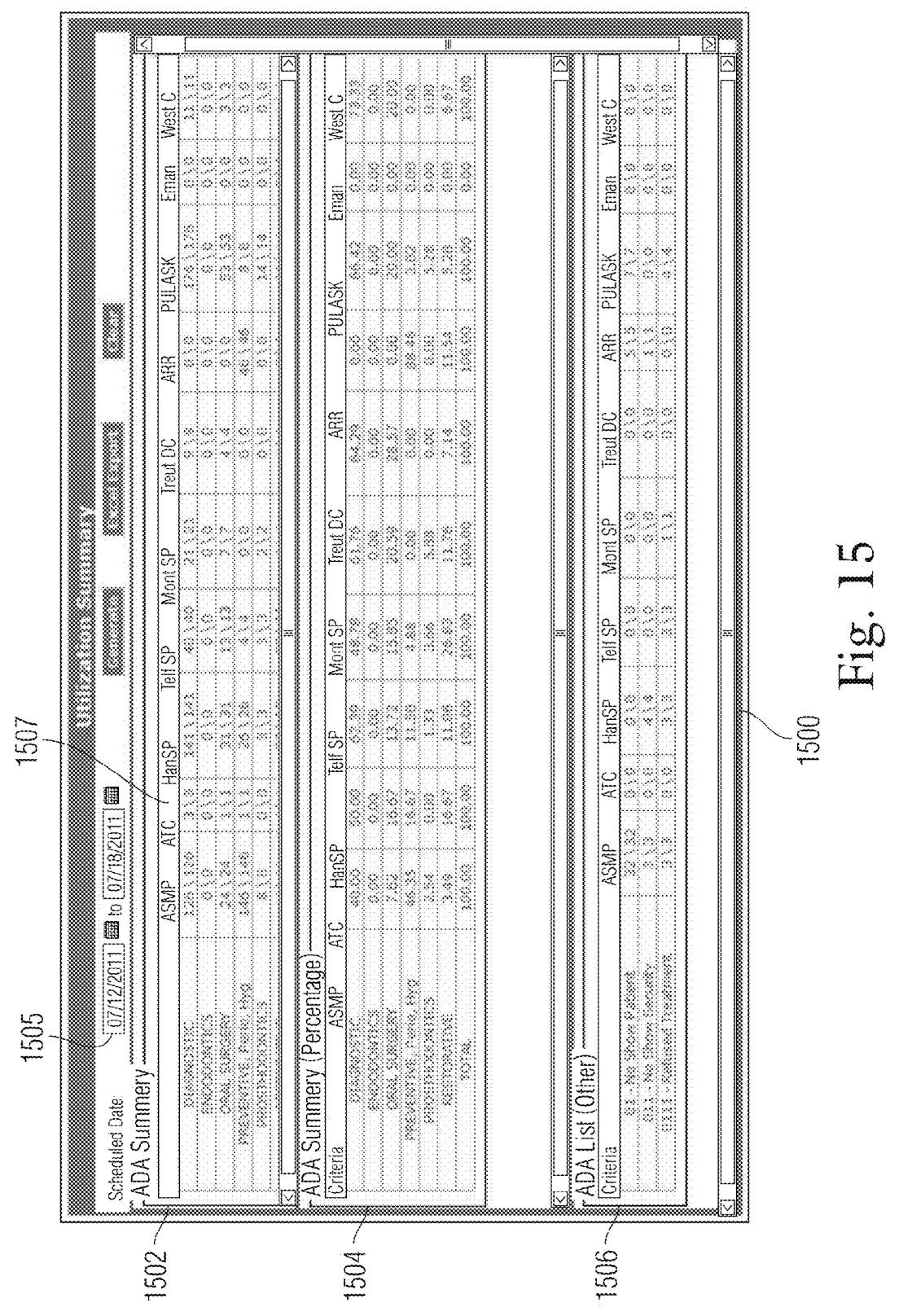

FIG. 15 depicts a graphical user interface of the Utilization Summary display 1500. A user may enter the Utilization Summary display 1500 through the Utilization Summary navigational button 516 on the homepage 500 as described in FIG. 5.

The Utilization Summary display 1500 includes the ADA Summary 1502, ADA Summary by percentage 1504, and ADA List 1506 with information for the different prison facilities 1507. The ADA Summary 1502 allows users to view statistics based on the type of procedures performed. The first number in the data displayed shows the total number of procedures performed over the date period set by the date range 1505 and the second number shows the average number of procedures over the date period set by the date range 1505 for each procedure displayed in window 1502.

Tithe ADA Summary (Percentage) 1504 displays the same statistics found in the ADA Summary 1502 but in a percentage format. The ADA List (Other) 1506 allows the user to view the statistics for the number of no show patients, no show because of security, and number of patients that refused treatment. A user may also view the statistics for a specified time period 1505 and export all data to an excel or similar type document.

By way of example, a facility supervisor may use the Utilization Summary display 1500 to effectively manage multiple facilities by viewing utilization summaries for each facility in a condensed format.

Figure 16:
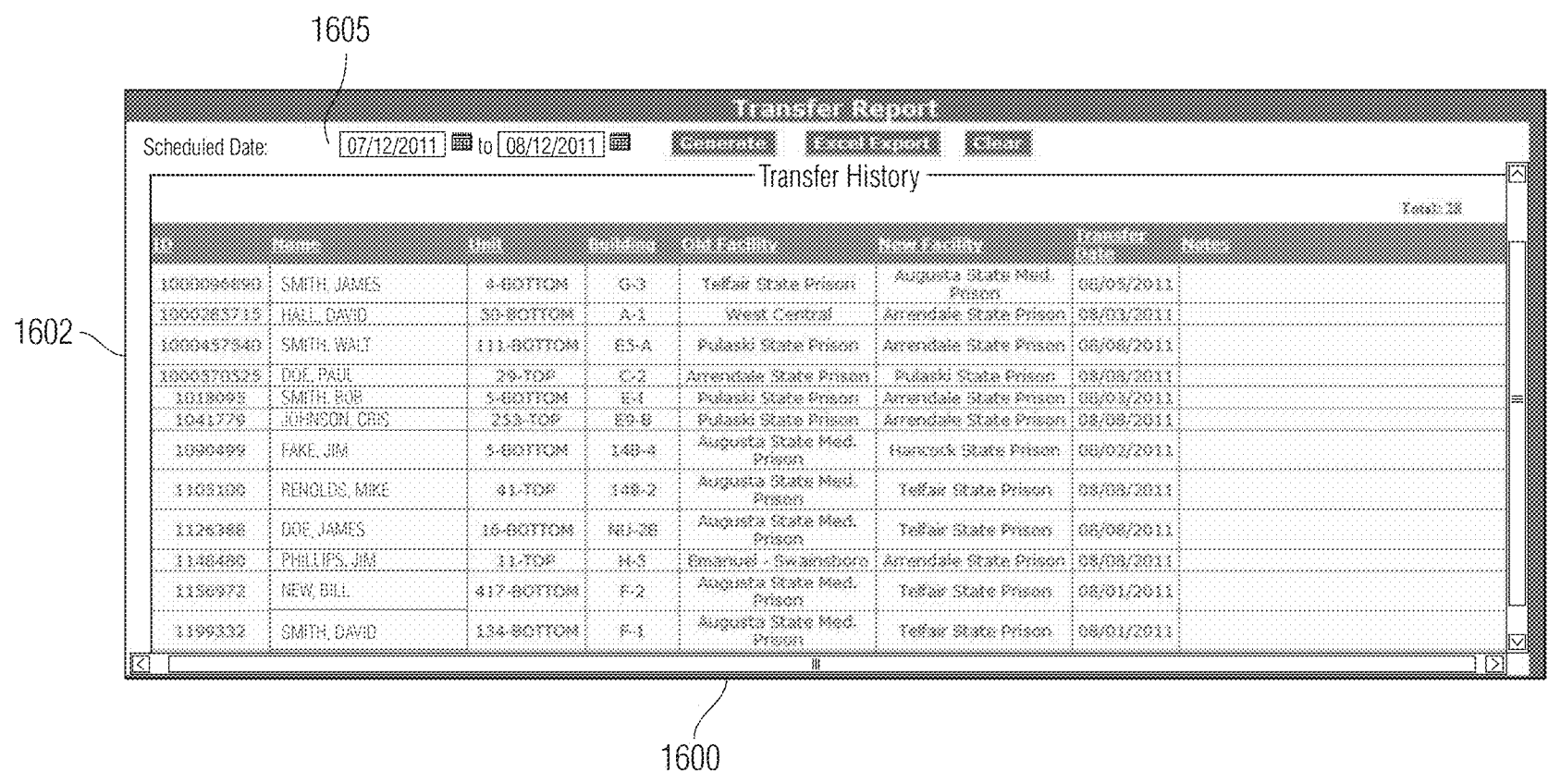

FIG. 16 depicts a graphical user interface for Transfer Report display 1600 including transfer history. A user may enter the Transfer Report display 1600 through the Transfer Report navigational button 518 on the homepage 500 as described in FIG. 5.

The Transfer Report display 1600 allows a user to view the transfer history 1502 of a patient, and also displays the patient identification number, name, unit, building, old facility, new facility, transfer date, and any notes. A user may also view the statistics for a specified time period 1605 and export an excel document of the statistics generated.

By way of example, a facility supervisory may use the Transfer Report display 1600 to generate a transfer report, and track where and when patients are transferred.

Figure 17:
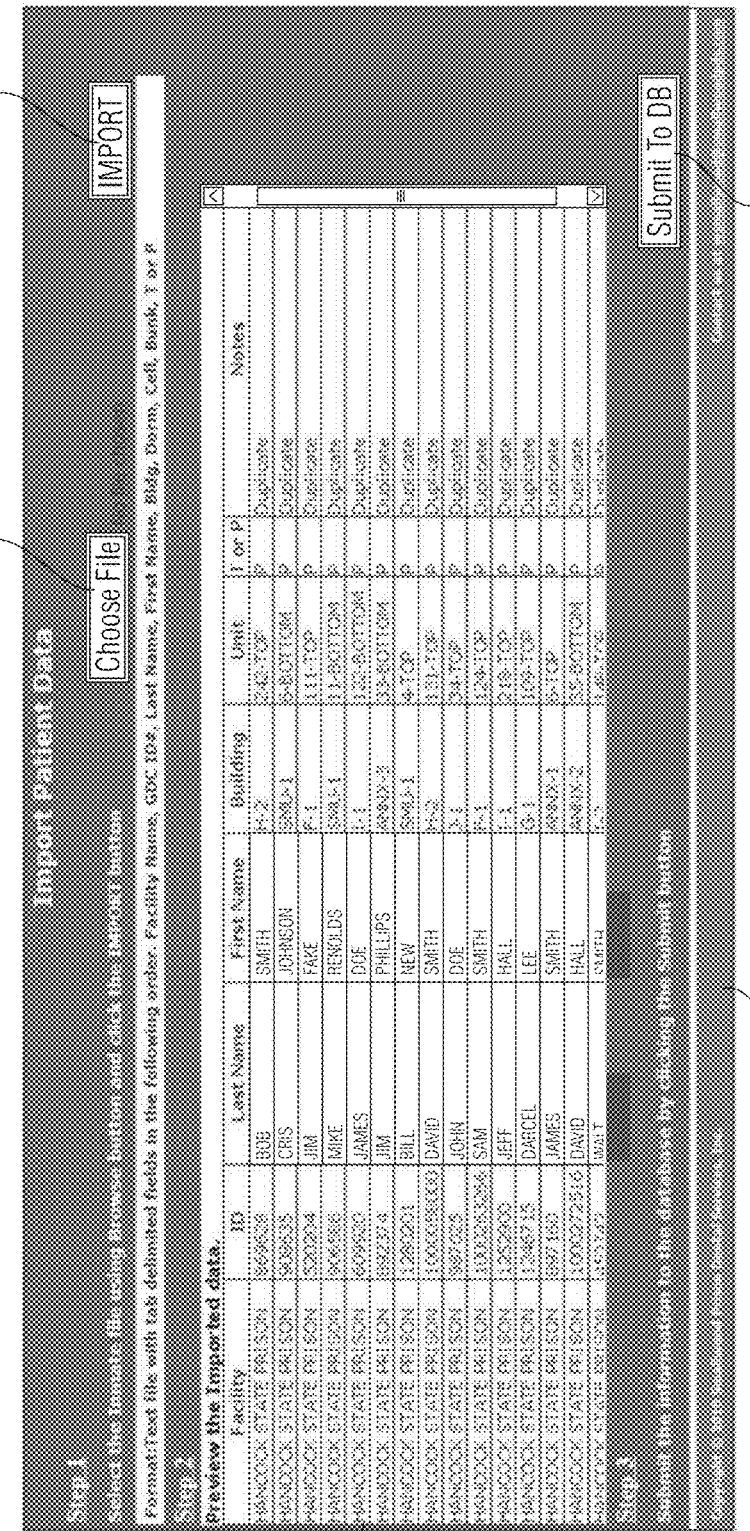
FIG. 17 illustrates a graphical user interface for the Import Patient Data display in accordance with the present invention.

FIG. 17 depicts a graphical user interface for the Import Patient Data display 1700 including file importing, previewing, and submission. A user may enter the Import Patient Data display 1700 through the Import Patient Data navigational button 520 on the homepage 500 as described in FIG. 5.

The Import Patient Data display 1700 allows a user to electronically transport a facility's bed log into the patient management database. The user selects a file to be imported using the Choose File button 1701 and imports the data using the Import button 1703. The imported data is displayed 1705 for the user's verification, and submitted into the database by clicking the Submit button 1707. This is completed on a daily basis to ensure the system knows who is present and who is not.

By way of example, an administrative user may avoid manually entering a patient's information into the patient management database as described in FIG. 6 by importing the patient's data using the Import Patient Data display 1700.

Figure 18:
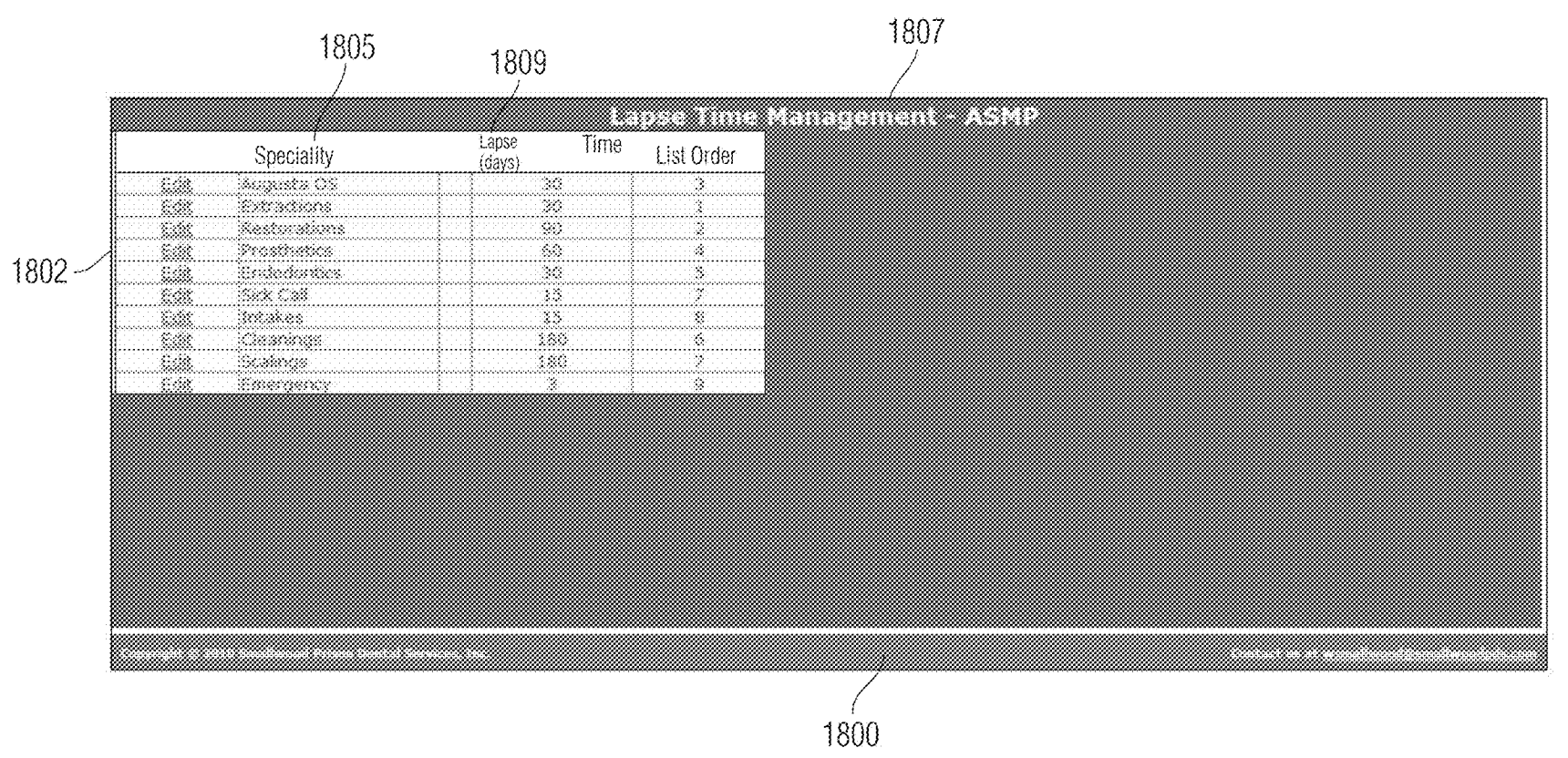

FIG. 18 depicts a graphical user interface for the Lapse Time Management 1800 for an individual prison facility 1807 including the item's specialty, lapse time, and list order. A user may enter the Lapse Time Management display 1800 through the Lapse Time Management navigational button 522 on the homepage 500 as described in FIG. 5.

The Lapse Time Management display 1800 lists the lapse time 1809 for each specialty 1805 in a display box 1802. This Lapse Time Management display 1800 also allows users to view and edit the lapse time for respective disciplines of dentistry.

By way of example, the a facility supervisor my use the Lapse Time Management display 1800 to edit the requirement time for each specialty in accordance to the established state law or organizations.

Figure 19:
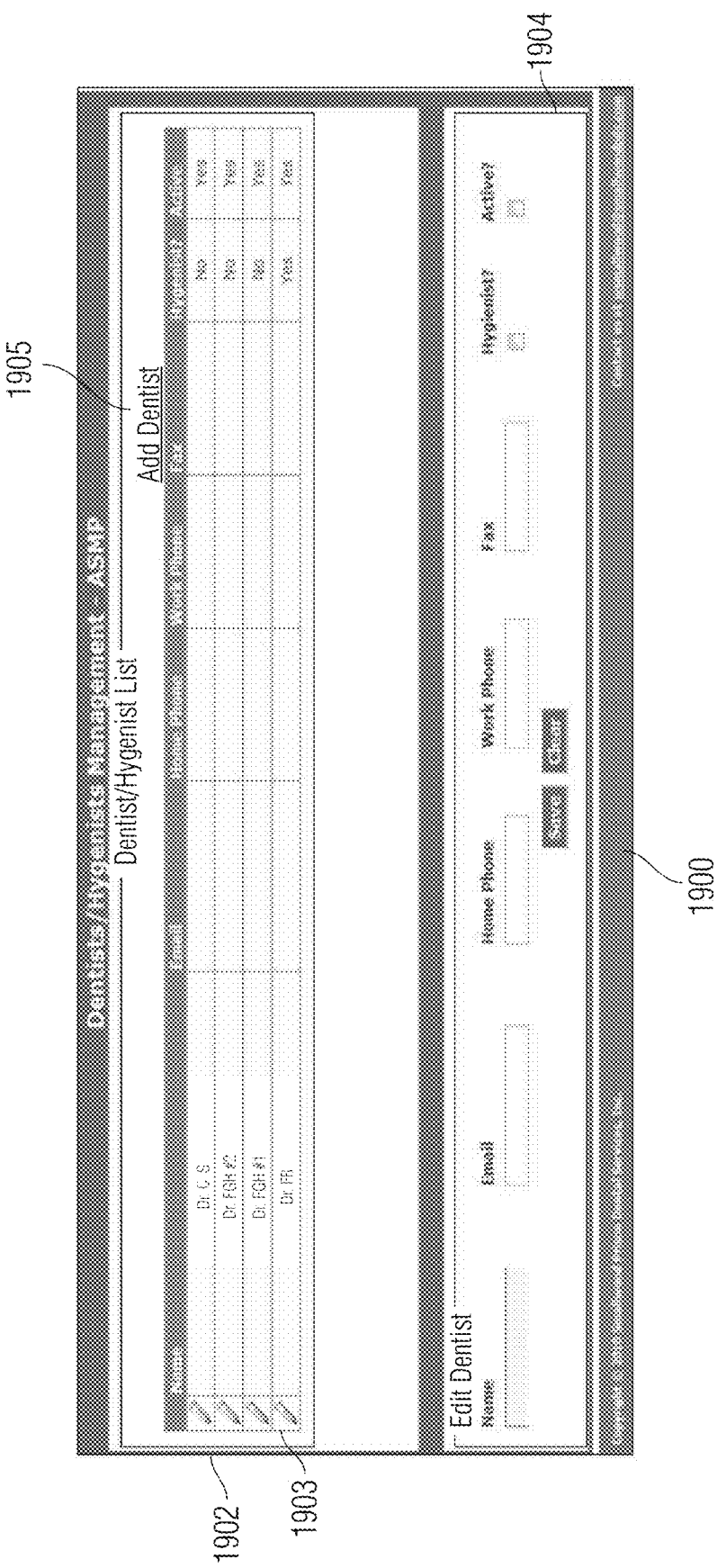
FIG. 19 illustrates a graphical user interface of the Dentists and Hygienists Management display in accordance with the present invention.

FIG. 19 depicts a graphical user interface of the Dentist Administration/Dentists/Hygienists Management—Facility display 1900 including the professional's name, email, home phone, work phone, fax number, specialty type, and activity status along with a field for editing dentist information. A user may enter the Dentists/Hygienists Management display 1900 through the Dentist Administration navigational button 524 on the homepage 500 as described in FIG. 5.

The Dentists/Hygienists display 1900 lists all dentists and hygienists at an individual prison facility whom are licensed to treat patients in a display box 1902. A user may edit a dentist's or hygienist's information by clicking on the "pencil" 1903 located next to the dentists or hygienists name. By clicking on the "pencil," the dentist's or hygienist's name will automatically populated in the Edit Dentist section 1904, and the user may then edit the dentist or hygienist information. A user may also add dentists or hygienists by clicking on the Add Dentist link 1905. By way of example, the administrative user may use the Dentists/Hygienists display 1900 to view the names of dentists and hygienists available for scheduling, edit dentist or hygienist information, and add dentists and hygienists.

Although the interface for the User Administration 526 (FIG. 5) is not depicted, the system provides the ability for a super administrator to set appropriate user levels and access controls of the various users and user levels. Thus, the system administrator can create different access levels for Senior Management, facility management, dentists, hygienists, and dental assistance. The system administrator can allow Senior Management access to certain management and reporting functional capabilities that a dental assistant, dentist, or hygienist would not have access to. Vice versa, the system may allow dental assistants, dentists and hygienists access to scheduling controls that the Senior Management would not have access to.

As a secondary embodiment, not depicted in FIGS. 5-19, the system will automatically create requests and effectively schedule appointments based on specified requirements dates, length of time it takes to perform a dental procedure, the availability of the dentist or hygienist, and the inmate's date of release as described in FIG. 4.

The examples provided herein are merely for the purpose of explanation and are in no way to be construed as limiting of the present method and product disclosed herein. While the invention has been described with reference to various embodiments, it is understood that the words which have been used herein are words of description and illustration, rather than words of limitation. Further, although the invention has been described herein with reference to particular means, materials, and embodiments, the invention is not intended to be limited to the particulars disclosed herein; rather, the invention expands to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention.

What is claimed is:

1. A system comprising:
a server with one or more computer programs, the server comprises a memory, the server configured to execute the one or more computer programs stored in the memory to perform processing, and the processing including the server:
receives and saves information to a first database on a periodic basis on a plurality of inmates in a first prison facility that is associated with the first database, the receiving of information being performed via an electronic communication path; the information including:
an inmate identification element for each inmate within the first prison facility and a prison facility identifier for each inmate within the first prison facility, and
a request procedure type for each inmate within the first prison facility that has requested a dental related procedure, and
a request date for each inmate within the first prison facility that has requested a dental related procedure;
tracks the lapsed time of each dental related request for each inmate starting from the request date to monitor compliance with the at least one time based rule, the at least one time based rule is based on the procedure type of the dental related procedure, and
the tracks the lapsed time is performed by the server using the inmate identification element and the prison facility identifier;
ranks the inmates within the first prison facility for scheduling of the dental related procedure based on the procedure type and lapsed time;
generates a first schedule to schedule the dental related procedures based on the ranking;
imports inmate transfer information from a second database into the first database, and
the second database associated with a second prison facility, and
the inmate transfer information includes data regarding inmates transferred from the second prison facility to the first prison facility;
inputs a second set of received information from the first database to identify inmates, within the first prison facility, which have a prison facility identifier change indicating the inmate has changed prison facilities from the second prison facility to the first prison facility as reflected in the imported inmate transfer information, and
the inputting of the second set of received information being performed via the electronic communication path;
updates the ranking of inmates within the first prison facility for scheduling of the dental related procedure based on the procedure type, available time slots, and the lapsed time, and wherein the procedure type, available time slots, and the lapsed time all being saved in the first database,
the updates the ranking of inmates including the server (i) comparing time allocated for each dental related procedure with available time slots, and (ii) providing priority to inmates based on lapsed time associated with each inmate;
generates a second schedule to schedule the dental related procedures based on the updated ranking and available time slots;
performs processing to determine lapsed times associated with the second schedule;
saves the second schedule in the memory; and
outputs the second schedule via the electronic communication path; and
wherein the providing priority to inmates based on lapsed time associated with each inmate affords that the inmates which have transferred from the second prison facility to the first prison facility maintain their original dental related procedure request date from the second prison facility; and
the server further generating a graphical user interface (GUI) of a physical user device, the GUI including an electronic management summary display that includes criteria aggregated of both (a) the first database associated with the first prison facility and (b) the second database associated with the second prison facility, and wherein the criteria in the management display summary including: (a) number of patients in the first prison facility and the second prison facility, (b) scheduled requests in the first prison facility and the second prison facility, and (c) requests not scheduled in the first prison facility and the second prison facility; and
wherein the management summary display aggregates data from the first database and data from the second database to provide for effective management of multiple prison facilities;
the server performing further processing including:
monitoring when a lapsed time, of a particular inmate, exceeds the time based rule by comparing the lapsed time, of the particular inmate, with the time based rule;
identifying that a lapsed time has exceeded the time based rule for an inmate;
controlling the outputting of an alert, in the form of a physical representation displayed to the user on the GUI, indicating the lapsed time exceeds the time based rule for the inmate, and the alert is constituted by an identifier visually displayed on the GUI such that the server interfaces with a human user interacting with the system;
performing a physical step of treating a patient based on the alert, which is displayed upon the GUI of the physical user device, and the treating the patient including performing a dental related procedure on the patient;
the server performing further processing including:
interfacing with the human via the GUI to receive input that the human user has physically selected an inmate's name;

activating, in response to such received input, a request management display that includes a new request with the inmate's name;

interfacing with the human via the GUI to receive input with particulars of the new request so as to populate the new request, interfacing with the human via the GUI to receive input, via the human user's physical manipulation of a button on the GUI, to physically control movement of the new request from an unscheduled request display to a scheduled request display so as to schedule the new request; and wherein the new request constitutes one of the dental related requests.

2. The system of claim 1, wherein the at least one time based rule is the number of days from the request date by which a procedure should be performed based on the procedure type.

3. The system of claim 2, wherein the number of days is set by an administrative user of the system.

4. The system of claim 1, wherein data related to the identified and ranked inmate for scheduling are transmitted, by the server, to a remote device for display to a user.

5. The system of claim 4, wherein the server provides processing such that the user can select at least one inmate to be added to a schedule.

6. The system of claim 1, wherein the server generates a further alert, the further alert is an email or text message sent to an identified address.

7. The system of claim 1, wherein the periodic basis for receiving information is daily.

8. The system of claim 1, wherein the server automatically generates a schedule of procedures based on the rankings.

9. A computer implemented method to monitor compliance with at least one time based rule, the method implemented on a server with one or more computer programs, the server comprises a memory, the server configured to execute the one or more computer programs stored in the memory to perform processing, and the method comprising:

(i) receiving and saving information to a first database on a periodic basis on a plurality of inmates within a group from at least one prison facility, wherein the information includes an identification element for each inmate within the at least one prison facility and a prison facility identifier for each inmate and a request procedure type and a request date for each inmates within the group that has requested a dental related procedure, and the receiving of information being performed via an electronic communication path, the information being saved in the memory;

(ii) assigning the at least one time based rule to each dental related request for each inmates; wherein the at least one time based rule is based on procedure type of the dental related procedure;

(iii) tracking the lapsed time of each dental related request for each individual starting from the request date; and the tracking the lapsed time is performed by the server using the identification element and the prison facility identifier;

(iv) ranking the inmates within the prison facility based on the procedure type and the lapse timed; and generates a first schedule to schedule the dental related procedures based on the ranking;

(v) inputs a second set of received information, from a second database of a second prison facility, to identify inmates which have a prison facility identifier change indicating the individual has changed facilities; and the inputs the second set of received information being performed via the electronic communication path;

(vi) updating the ranking of inmates within each at least one prison facility for scheduling of the dental related procedure based on the procedure type and the lapsed time; the procedure type and the lapsed time both being saved in the memory, the updating the ranking of inmates including the server (i) comparing time allocated for each dental related procedure with available time slots, and (ii) providing priority to inmates based on lapsed time associated with each inmate;

(vii) generates a second schedule to schedule the dental related procedures based on the updated ranking and available time slots;

(viii) performs processing to determine that there are no missed lapse times;

(ix) saves the second schedule in the memory; and (x) outputs the second schedule via the electronic communication path; and wherein the providing priority to inmates based on lapsed time associated with each inmate affords that the inmates which have transferred facilities maintain their original dental related procedure request date; and the server further generating a graphical user interface (GUI) of a physical user device, the GUI including an electronic management summary display that includes criteria aggregated of both (a) the first database associated with the first prison facility and (b) the second database associated with the second prison facility, and wherein the criteria in the management display summary including: (a) number of patients in the first prison facility and the second prison facility, (b) scheduled requests in the first prison facility and the second prison facility, and (c) requests not scheduled in the first prison facility and the second prison facility; and wherein the management summary display aggregates data from the first database and data from the second database to provide for effective management of multiple prison facilities;

the server performing further processing including:

monitoring when a lapsed time, of a particular inmate, exceeds the time based rule by comparing the lapsed time, of the particular inmate, with the time based rule;

identifying that a lapsed time has exceeded the time based rule for an inmate;

controlling the outputting of an alert, in the form of a physical representation displayed to the user on the GUI, indicating the lapsed time exceeds the time based rule for the inmate, and the alert is constituted by an identifier visually displayed on the GUI such that the server interfaces with a human user interacting with the system;

performing a physical step of treating a patient based on the alert, which is displayed upon the GUI of the physical user device, and the treating the patient including performing a dental related procedure on the patient;

the server performing further processing including:

interfacing with the human via the GUI to receive input that the human user has physically selected an inmate's name;

activating, in response to such received input, a request management display that includes a new request with the inmate's name;

interfacing with the human via the GUI to receive input with particulars of the new request so as to populate the new request, interfacing with the human via the GUI to receive input, via the human user's physical manipulation of a button on the GUI, to physically control movement of the new request from an unscheduled request display to a scheduled request display so as to schedule the new request; and wherein the new request constitutes one of the dental related requests.

10. The method of claim 9, wherein the at least one time based rule is the number of days from the request date by which a procedure should be performed based on the procedure type.

11. The method of claim 10, further including the server setting the number of days based on input received from an administrative user of the system.

12. The method of claim 9, further including the step of the server tracking the schedule of a medical professional wherein the schedule includes available and unavailable time slots.

13. The method in claim 12, wherein the server providing for the user to set time slots on the schedule as unavailable.

14. The method of claim 13, further including the step of the server scheduling the inmates based on the rank, procedure type, and available time slots.

15. The method of claim 14, further including the step of the server automatically generating a schedule of procedures based on the rankings.

16. The method of claim 15, further including the step of the server transmitting data related to the identified and ranked inmates for scheduling to a remote device for display to a user.

17. The method of claim 16, wherein the server provides processing such that the user monitors and tracks the patient information, the lapse time for each dental related request, and the scheduled inmates using a remote device.

18. The method of claim 17, further including the step of the server receiving an input from the user for the selection of an inmate to be added to the schedule.

19. The method of claim 9, wherein the server generates a further alert, the further alert is an email or text message sent to an identified address.

20. The method of claim 9, wherein the periodic basis for receiving information is daily.

21. A computer implemented method, the method implemented on a server with one or more computer programs, the server comprises a memory, the server configured to execute the one or more computer programs stored in the memory to perform processing, and the method comprising:

(i) receiving information, and saving such information to a first database, on a periodic basis on a plurality of individuals within a group from at least one facility, wherein the information includes an identification element for each individual within the group and a facility identifier for each individual within the group, and a request procedure type and a request date for each individual within the group that has requested a health related procedure, the receiving information being performed via an electronic communication path, the information being saved in the memory;

(ii) assigning the at least one time based rule to each health related request for each individual; wherein the at least one time based rule is based on procedure type of the health related procedure;

(iii) tracking the lapsed time of each health related request for each individual starting from the request date to monitor compliance with the at least one time based rule; wherein the at least one time based rule is based on the procedure type; and the tracking the lapsed time is performed by the server using the inmate identification element and the prison facility identifier;

(iv) ranking the individuals within each facility based on the procedure type and lapsed time; and generates a first schedule to schedule the health related procedures based on the ranking;

(v) determining a set of individuals within each facility for scheduling of the health related procedure based on the procedure type and lapsed time;

(vi) inputs a second set of received information, from a second database of a second prison facility, to identify individuals within the group which have a facility identifier change indicating the individual has changed facilities; and the inputs the second set of received information being performed via the electronic communication path;

(vii) identifying individuals within the group which have a facility identifier change indicating the individual has changed facilities; and (viii) updating the ranking of individuals within each facility for scheduling of the health related procedure based on the lapsed time and the at least one time based rule; the procedure type and the lapsed time both being saved in the memory, and the updating the ranking of individuals including the server (i) comparing time allocated for each health related procedure with available time slots, and (ii) providing priority to individuals based on lapsed time associated with each inmate;

(ix) generates a second schedule to schedule the health related procedures based on the updated ranking and available time slots;

(x) performs processing to determine that there are no missed lapse times;

(xi) saves the second schedule in the memory; and (xii) outputs the second schedule via the electronic communication path; and wherein the providing priority to individual based on lapsed time associated with each individual affords that the individuals which have transferred facilities maintain their original health related procedure request date;

the server further generating a graphical user interface (GUI) of a physical user device, the GUI including an electronic management summary display that includes criteria aggregated of both (a) the first database associated with the first prison facility and (b) the second database associated with the second prison facility, and wherein the criteria in the management display summary including: (a) number of patients in the first prison facility and the second prison facility, (b) scheduled requests in the first prison facility and the second prison facility, and (c) requests not scheduled in the first prison facility and the second prison facility; and wherein the management summary display aggregates data from the first database and data from the second database to provide for effective management of multiple prison facilities;

the server performing further processing including:

monitoring when a lapsed time, of a particular inmate, exceeds the time based rule by comparing the lapsed time, of the particular inmate, with the time based rule;

identifying that a lapsed time has exceeded the time based rule for an inmate;
controlling the outputting of an alert, in the form of a physical representation displayed to the user on the GUI, indicating the lapsed time exceeds the time based rule for the inmate, and the alert is constituted by an identifier visually displayed on the GUI such that the server interfaces with a human user interacting with the system;
the server performing further processing including:
interfacing with the human via the GUI to receive input that the human user has physically selected an inmate's name;
activating, in response to such received input, a request management display that includes a new request with the inmate's name;
interfacing with the human via the GUI to receive input with particulars of the new request so as to populate the new request,
interfacing with the human via the GUI to receive input, via the human user's physical manipulation of a button on the GUI, to physically control movement of the new request from an unscheduled request display to a scheduled request display so as to schedule the new request; and
wherein the new request constitutes one of the dental related requests; and
the method further including performing a physical step of treating a patient based on the alert, which is displayed upon the GUI of the physical user device, and the treating the patient including performing a dental related procedure on the patient.

22. A computing device, comprising:
a processor coupled to a non-transitory, computer readable storage medium having stored thereon computer executable instructions for a patient ranking software application that is used in scheduling a plurality of prison patients for a dental procedure, the software application, when executed by the processor, configuring the processor to:
receive and save a plurality of information, from a first database, on a periodic basis on a plurality of prison patients awaiting a dental procedure within at least one prison facility, the receiving of information being performed via an electronic communication path, the information being saved in the computer readable storage medium;
analyze the plurality of information, resident on the storage medium, on a plurality of prison patients awaiting a dental procedure, wherein the information includes a patient identifier for each prison patient within the at least one prison facility, a facility identifier for each prison patient within the at least one prison facility, a request procedure type, and a request date for each individual within the plurality of prison patients;
track the lapsed time of each dental procedure request from the request date to monitor compliance with at least one time based rule; wherein the at least one time based rule is based on the procedure type of the dental procedure; and the tracking the lapsed time is performed by the processor using the patient identifier and the facility identifier
rank the plurality of prison patients for scheduling based on the procedure type and lapsed time to create an initial ranked list; and generates a first schedule to schedule the dental procedures based on the ranking;
receive, from a first remote device, a set of prison inmate transfer data;
inputs a second set of information, from a second database of a second prison facility, including prison inmate transfer data to identify prison inmates which have a facility identifier change; the inputs the second set of information being performed via the electronic communication path;
update the ranking of prison patients to create an updated ranked list based on the procedure type and the lapsed time; the procedure type and the lapsed time both being saved in the memory,
the update the ranking of prison patients including the processor (i) comparing time allocated for each dental procedure with available time slots, and (ii) providing priority to patients based on lapsed time associated with each patient;
generates a second schedule to schedule the dental procedures based on the updated ranking and available time slots;
performs processing to determine that there are no missed lapse times; transmit the updated ranked list, to a second remote device associated with a prison facility, for display on the second remote device;
receiving, from the second remote device, a schedule of scheduled prison inmates selected from the updated ranked list;
saving, on the storage medium, the schedule
wherein the providing priority to patients based on lapsed time associated with each patient affords that the patients which have transferred facilities maintain their original dental procedure request date; and
the server further generating a graphical user interface (GUI) of a physical user device, the GUI including an electronic management summary display that includes criteria aggregated of both (a) the first database associated with the first prison facility and (b) the second database associated with the second prison facility, and wherein the criteria in the management display summary including: (a) number of patients in the first prison facility and the second prison facility, (b) scheduled requests in the first prison facility and the second prison facility, and (c) requests not scheduled in the first prison facility and the second prison facility; and
wherein the management summary display aggregates data from the first database and data from the second database to provide for effective management of multiple prison facilities;
the server performing further processing including:
monitoring when a lapsed time, of a particular inmate, exceeds the time based rule by comparing the lapsed time, of the particular inmate, with the time based rule;
identifying that a lapsed time has exceeded the time based rule for an inmate;
controlling the outputting of an alert, in the form of a physical representation displayed to the user on the GUI, indicating the lapsed time exceeds the time based rule for the inmate, and the alert is constituted by an identifier visually displayed on the GUI such that the server interfaces with a human user interacting with the system;
performing a physical step of treating a patient based on the alert, which is displayed upon the GUI of the physical user device, and the treating the patient including performing a dental related procedure on the patient;

the server performing further processing including:
  interfacing with the human via the GUI to receive input that the human user has physically selected an inmate's name;
  activating, in response to such received input, a request management display that includes a new request with the inmate's name;
  interfacing with the human via the GUI to receive input with particulars of the new request so as to populate the new request,
  interfacing with the human via the GUI to receive input, via the human user's physical manipulation of a button on the GUI, to physically control movement of the new request from an unscheduled request display to a scheduled request display so as to schedule the new request; and
  wherein the new request constitutes one of the dental related requests.

23. A non-transitory, computer-readable storage medium having stored thereon computer executable instructions that enable operation of a patient ranking software module used in scheduling appointments for a prison facility, the computer-executable instructions comprising:
  a processor coupled to a non-transitory, computer readable storage medium having stored thereon computer executable instructions for a patient ranking software application for use in scheduling a plurality of prison patients for a dental procedure, the software application, when executed by the processor, configuring the processor to:
    receive and save a plurality of information, on a first database of a first prison facility, on a periodic basis on the plurality of prison patients for the first prison facility, the receiving of information being performed via an electronic communication path, the information being saved in the storage medium;
    analyze the plurality of information, resident on the storage medium, on a plurality of prison patients awaiting a dental procedure, wherein the information includes a patient identifier for each individual within the plurality of prison patients, a facility identifier for each individual within the plurality of prison patients, a request procedure type for each individual within the plurality of prison patients, and a request date for each individual within the plurality of prison patients;
    track the lapsed time of each dental procedure request from the request date to monitor compliance with at least one time based rule; wherein the at least one time based rule is based on the procedure type of the dental procedure; the track the lapsed time is performed by the processor using the patient identifier and the facility identifier;
    rank the plurality of prison patients for scheduling based on the procedure type and lapsed time to create an initial ranked list; and generates a first schedule to schedule the dental procedures based on the ranking;
    receive a second set of data, disposed on a second database of a second prison facility, including a set of prison inmate transfer data;
    compare the prison inmate transfer data against the ranked list or prison patients to identify prison inmates which have a facility identifier change;
    update the ranking of prison patients based on the transfer data to create an updated ranked list based on the procedure type and the lapsed time; the procedure type and the lapsed time both being saved in the storage medium,
      the update the ranking of prison patients including the processor (i) comparing time allocated for each dental procedure with available time slots, and (ii) providing priority to prison patients based on lapsed time associated with each prison patient;
    generate a second schedule to schedule the dental procedures based on the updated ranking and available time slots;
    perform processing to determine that there are no missed lapse times;
    transmit the updated ranked list, to a remote device associated with a prison facility, for display on the remote device;
    receiving, from the remote device, a schedule of scheduled prison inmates selected from the updated ranked list;
    saving, on the storage medium, the schedule; and
    wherein the providing priority to prison patients based on lapsed time associated with each prison patient affords that the prison patients which have transferred facilities maintain their original dental procedure request date; and
  the server further generating a graphical user interface (GUI) of a physical user device, the GUI including an electronic management summary display that includes criteria aggregated of both (a) the first database associated with the first prison facility and (b) the second database associated with the second prison facility, and wherein the criteria in the management display summary including: (a) number of patients in the first prison facility and the second prison facility, (b) scheduled requests in the first prison facility and the second prison facility, and (c) requests not scheduled in the first prison facility and the second prison facility; and
    wherein the management summary display aggregates data from the first database and data from the second database to provide for effective management of multiple prison facilities;
  the server performing further processing including:
    monitoring when a lapsed time, of a particular inmate, exceeds the time based rule by comparing the lapsed time, of the particular inmate, with the time based rule;
    identifying that a lapsed time has exceeded the time based rule for an inmate;
    controlling the outputting of an alert, in the form of a physical representation displayed to the user on the GUI, indicating the lapsed time exceeds the time based rule for the inmate, and the alert is constituted by an identifier visually displayed on the GUI such that the server interfaces with a human user interacting with the system;
  performing a physical step of treating a patient based on the alert, which is displayed upon the GUI of the physical user device, and the treating the patient including performing a dental related procedure on the patient;
  the server performing further processing including:
    interfacing with the human via the GUI to receive input that the human user has physically selected an inmate's name;
    activating, in response to such received input, a request management display that includes a new request with the inmate's name;

interfacing with the human via the GUI to receive input with particulars of the new request so as to populate the new request, interfacing with the human via the GUI to receive input, via the human user's physical manipulation of a button on the GUI, to physically control movement of the new request from an unscheduled request display to a scheduled request display so as to schedule the new request; and wherein the new request constitutes one of the dental related requests.

* * * * *

UNITED STATES PATENT AND TRADEMARK OFFICE
CERTIFICATE OF CORRECTION

| | |
|---|---|
| PATENT NO. | : 9,875,514 B2 |
| APPLICATION NO. | : 13/287591 |
| DATED | : January 23, 2018 |
| INVENTOR(S) | : William Smallwood |

It is certified that error appears in the above-identified patent and that said Letters Patent is hereby corrected as shown below:

On the Title Page

Inventor added:
Vijay Anand Sivaprakasam, of Aldie, Virginia is added as an inventor.

Signed and Sealed this
Thirty-first Day of January, 2023

Katherine Kelly Vidal
*Director of the United States Patent and Trademark Office*